United States Patent
Dufresne et al.

(10) Patent No.: US 8,594,339 B2
(45) Date of Patent: Nov. 26, 2013

(54) POWER MANAGEMENT FOR MEDICAL SENSING DEVICES EMPLOYING MULTIPLE SENSOR SIGNAL FEATURE DETECTION

(75) Inventors: Joel R. Dufresne, St. Paul, MN (US); Hatim M. Carim, West St. Paul, MN (US); Thomas E. Drummond, Stillwater, MN (US)

(73) Assignee: 3M Innovative Properties Company, St. Paul, MN (US)

(*) Notice: Subject to any disclaimer, the term of this patent is extended or adjusted under 35 U.S.C. 154(b) by 1106 days.

(21) Appl. No.: 12/052,295

(22) Filed: Mar. 20, 2008

(65) Prior Publication Data
US 2008/0232604 A1   Sep. 25, 2008

Related U.S. Application Data

(60) Provisional application No. 60/919,574, filed on Mar. 23, 2007.

(51) Int. Cl.
  *A61B 7/04* (2006.01)
  *A61B 7/02* (2006.01)
  *H04R 25/00* (2006.01)

(52) U.S. Cl.
  USPC .............................. 381/67; 381/384; 181/131

(58) Field of Classification Search
  USPC ..................... 381/67, 74, 384, 71.7; 600/528; 181/131
  See application file for complete search history.

(56) References Cited

U.S. PATENT DOCUMENTS

| | | | |
|---|---|---|---|
| 3,862,379 A | 1/1975 | Pless | |
| 3,906,160 A | 9/1975 | Nakamura et al. | |
| 4,254,302 A | 3/1981 | Walshe | |
| 4,534,058 A | 8/1985 | Hower | |

(Continued)

FOREIGN PATENT DOCUMENTS

| | | |
|---|---|---|
| CN | 1946345 A | 4/2007 |
| DE | 10164758 | 5/2004 |

(Continued)

OTHER PUBLICATIONS

Houtsma et al., "A Noise-Immune Stethoscope for Use in Noisy Environments," 4$^{th}$ ASA/ASJ Joint Meeting, Honolulu, HI, Dec. 2, 2006, pp. 1-6; retrieved from the Internet on Aug. 14, 2008 <URL:http://www.acoustics.org/press/152nd/houtsma.html>.

(Continued)

*Primary Examiner* — Daniel Luke
*Assistant Examiner* — Khaja Ahmad
(74) *Attorney, Agent, or Firm* — Ann K. Gallagher

(57) ABSTRACT

Power management circuitry of a portable electronic biosensor implements conditional power management logic to control biosensor power usage and to discriminate between intended use and nonuse of the biosensor by a clinician. The biosensor is configured to sense a property of the human body, such as a manifestation of acoustic energy produced by matter of biological origin or an action potential of the human body. An output signal is produced that is representative of the sensed property. A sensor of the biosensor produces a signal having a plurality of sensor signal features that are received by a detector of the power management circuitry. The power management circuitry or a processor of the biosensor discriminates between intended use and nonuse of the biosensor by the clinician using the sensor signal features. Power supplied to biosensor components is controlled based on the sensor signal features.

40 Claims, 15 Drawing Sheets

(56) References Cited

U.S. PATENT DOCUMENTS

| | | | |
|---|---|---|---|
| 4,618,986 A | 10/1986 | Hower | |
| 4,723,555 A | 2/1988 | Shue | |
| 4,878,501 A | 11/1989 | Shue | |
| 5,027,825 A | 7/1991 | Phelps et al. | |
| 5,467,775 A | 11/1995 | Callahan et al. | |
| 5,492,129 A | 2/1996 | Greenberger | |
| 5,701,904 A | 12/1997 | Simmons et al. | |
| 5,708,725 A | 1/1998 | Ito | |
| 5,812,678 A * | 9/1998 | Scalise et al. | 381/67 |
| 5,825,895 A | 10/1998 | Grasfield | |
| 5,832,093 A | 11/1998 | Bernstein | |
| 5,960,089 A | 9/1999 | Bouricius et al. | |
| 6,005,951 A | 12/1999 | Grasfield et al. | |
| 6,028,942 A | 2/2000 | Greenberger | |
| 6,083,156 A | 7/2000 | Lisiecki | |
| 6,533,736 B1 | 3/2003 | Moore | |
| 7,024,001 B1 | 4/2006 | Nakada | |
| 7,091,879 B2 | 8/2006 | Swetlik | |
| 7,593,534 B2 | 9/2009 | Andersen | |
| 7,636,445 B2 | 12/2009 | Yoshimine | |
| 7,806,226 B2 | 10/2010 | Drummond | |
| 2002/0055684 A1 | 5/2002 | Patterson | |
| 2003/0002685 A1* | 1/2003 | Werblud | 381/67 |
| 2004/0116969 A1* | 6/2004 | Owen et al. | 607/6 |
| 2004/0228494 A1 | 11/2004 | Smith | |
| 2005/0058298 A1 | 3/2005 | Smith | |
| 2005/0119584 A1 | 6/2005 | Carter | |
| 2005/0119854 A1 | 6/2005 | Maier et al. | |
| 2005/0232434 A1 | 10/2005 | Andersen | |
| 2006/0005058 A1* | 1/2006 | Chen et al. | 713/320 |
| 2006/0260865 A1 | 11/2006 | Puder | |
| 2007/0076897 A1* | 4/2007 | Philipp | 381/74 |
| 2007/0106179 A1 | 5/2007 | Bagha et al. | |
| 2007/0113649 A1 | 5/2007 | Bharti et al. | |
| 2007/0113654 A1 | 5/2007 | Carim et al. | |
| 2008/0013747 A1 | 1/2008 | Tran | |
| 2008/0114248 A1* | 5/2008 | Urbano et al. | 600/447 |
| 2009/0052699 A1 | 2/2009 | Andersen | |

FOREIGN PATENT DOCUMENTS

| | | |
|---|---|---|
| WO | WO 97/03600 | 2/1997 |
| WO | 01/78604 | 10/2001 |
| WO | 2004/002191 | 12/2003 |
| WO | WO 2005/032212 | 4/2005 |
| WO | WO 2006/073854 A1 | 7/2006 |

OTHER PUBLICATIONS

VIASYS Healthcare Inc., "Nicolet StethoDop™ Vascular Doppler," 2 pages, 2004.

International Preliminary Report on Patentability for PCT/US2008/057691.

International Search Report for PCT/US2008/057691.

\* cited by examiner

POWER MANAGEMENT FOR MEDICAL SENSING DEVICES EMPLOYING MULTIPLE SENSOR SIGNAL FEATURE DETECTION

RELATED PATENT DOCUMENTS

This application claims the benefit of Provisional Patent Application Ser. No. 60/919574 filed on Mar. 23, 2007, to which priority is claimed pursuant to 35 U.S.C. §119(e) and which is hereby incorporated herein by reference.

FIELD OF THE INVENTION

The present invention relates to medical sensing devices and, more particularly, to biosensors and systems incorporating biosensors that employ conditional power management logic for controlling application and removal of power to and from biosensor components.

BACKGROUND

A variety of devices have been developed to detect sounds produced by the body, such as heart sounds and lung sounds. Known devices range from primarily mechanical devices, such as the stethoscope, to various electronic devices, such as microphones and transducers. The stethoscope, for example, is a fundamental tool used in the diagnosis of diseases and conditions of the cardiovascular system. It serves as the most commonly employed technique for diagnosis of such diseases and conditions in primary health care and in circumstances where sophisticated medical equipment is not available, such as remote areas.

Electronic stethoscopes offer the opportunity to enhance a clinician's ability to detect a variety of body sounds, and to distinguish between normal and abnormal patient conditions, such as benign and non-benign heart murmurs. Although many electronic stethoscopes are available on the market, they have yet to gain universal acceptance by the physicians and other medical practitioners. Possible reasons for slow acceptance of electronic stethoscopes include perceived differences in how the clinician interacts with an electronic stethoscope relative to a conventional mechanical stethoscope. For example, the simple task of activating an ON switch to enable usage of an electronic stethoscope may be viewed as an inconvenient and distracting action not required when using a conventional mechanical stethoscope.

SUMMARY OF THE INVENTION

The present invention is generally directed to managing power for an electronic biosensor or other portable electronic medical diagnostic devices. The present invention is directed more particularly to managing power based on sensing parameters or events that indicate a clinician's intent to use or not use a biosensor.

Embodiments of the present invention are directed to electronic biosensors comprising a housing configured for hand-held manipulation by a clinician. The biosensor includes a transducer supported by the housing and configured to sense a property of the human body, such as a manifestation of acoustic energy produced by matter of biological origin. The transducer of the biosensor may be configured to sense other properties of the human body, such as flow or volume of a fluid (e.g., a body fluid or air during inspiration/expiration), a biopotential (e.g., potentials generated during the excitation of nerve and muscle tissue), and a structural or compositional property of the human body (e.g., property of bone, such as bone density, soft tissue, organs, blood, blood gases and blood chemistry). An output device is configured to output a signal comprising signal information produced by the transducer. A processor and power management circuitry are disposed in the housing.

According to various embodiments, the power management circuitry is coupled to a sensor of the biosensor, and the power management circuitry comprises detection circuitry configured to detect a plurality of features of a signal produced by the sensor. The sensor preferably has a single sensing element that produces a sensor signal having a plurality of features that can be detected by a detector of the power management circuitry or the processor. Alternatively, the sensor may be configured as a single sensor or sensing device that incorporates multiple sensing elements having different excitation response characteristics. In some embodiments, the sensor is a sensing component distinct from a primary transducer of the biosensor. In other embodiments, the sensor comprises the primary transducer of the biosensor.

The power management circuitry is configured to implement conditional power management logic by which the power management circuitry discriminates between intended use and nonuse of the biosensor by the clinician using the plurality of sensor signal features. In other configurations, the power management circuitry determines readiness of the biosensor for immediate or imminent use by the clinician using the plurality of sensor signal features. The power management circuitry and the processor cooperate to control power supplied to biosensor components based on the plurality of sensor signal features.

Embodiments of the present invention are directed to methods of managing power in an electronic biosensor configured for hand-held manipulation by a clinician. Methods of the invention involve sensing a property of the human body, such as a manifestation of acoustic energy produced by matter of biological origin. An output signal is produced that is representative of the sensed property, such as the sensed manifestation of acoustic energy. Methods of the present invention involve receiving a sensor signal from a sensor of the biosensor, detecting a plurality of features of the sensor signal, and discriminating between intended use and nonuse of the biosensor by the clinician using sensor signal features. Power supplied to biosensor components is controlled based on the sensor signal features.

In accordance with other embodiments, the power management circuitry is coupled to at least a first sensor and a second sensor of the biosensor respectively configured to produce first and second sensor signals. The power management circuitry is configured to implement conditional power management logic by which the power management circuitry discriminates between intended use and nonuse of the biosensor by the clinician based on a state of the first and second sensor signals. In other configurations, the power management circuitry determines readiness of the biosensor for immediate or imminent use by the clinician based on a state of the first and second sensor signals. The power management circuitry and the processor cooperate to control power supplied to biosensor components based on the state of the first and second sensor signals.

One of the first and second sensors may include a sensor the produces an output indicative of sensor proximity to a body surface or clothing on the body. One of the first and second sensors may comprise a contact sensor. One of the first and second sensors may comprise the transducer of the biosensor. Each of the first and second sensors may comprise a sensor transducer other than the biosensor transducer. Each of the first and second sensors may comprises a transducer configured to sense a physiologic parameter of the human body. One of the first and second sensors may comprise a transducer configured to sense a physiologic parameter of the human body, and the other of the first and second sensors may comprise a transducer configured to sense a non-physiologic parameter. The first and second sensors may comprise a transducer configured to sense at least one of a flow or volume of a fluid, a transducer configured to sense a biopotential, and a transducer configured to sense a structural or compositional property of the human body. The transducer of the first sensor may differ from that of the second sensor in terms of sensed property of the human body. One of the first and second sensors may comprise the transducer, and the other of the first and second sensors may comprise an accelerometer.

The processor may be configured to transition from a low power mode to an operational power mode in response to the state of a predetermined one of the first and second sensor signals indicating intended use of the biosensor by the clinician as determined by the power management circuitry. The processor may be configured to transition from a low power mode to an operational power mode in response to the state of both the first and second sensor signals indicating intended use of the biosensor by the clinician as determined by the power management circuitry.

The power management circuitry may be configured to discriminate between intended use and nonuse of the biosensor by the clinician based at least in part on a comparison of at least one of the first and second sensor signals to a predefined sensor profile that characterizes an excitation response of the sensor. The power management circuitry may be configured to discriminate between intended use and nonuse of the biosensor by the clinician based on a temporal order of occurrence of the first and second sensor signals and/or a time duration between sensing of the first signal and sensing of the second sensor signal by the first and second sensors, respectively. The power management circuitry may be configured to disable implementation of some or all of the conditional power management logic in response to a command signal. The power management circuitry may implement or modify biosensor power management in accordance with a predefined power management profile selectable by the clinician. For example, the power management circuitry may implement or modify biosensor power management in accordance with an adaptive power management profile based on a history of biosensor power consumption.

A first power source may be coupled to the power management circuitry and define a low power source. The first power source may supply power for continuous or intermittent operation of the power management circuitry during a sleep state of the processor. A second power source may be coupled to the processor and define a high power source relative to the first power source. The second power source may supply power for the processor to transition the processor from the sleep state to a state that facilitates use of the biosensor by the clinician.

A user interface may be disposed on the housing of the biosensor. The user interface may comprise one of the first and second sensors. A headset may be configured to communicatively couple to the output device and convert the signal comprising signal information produced by the transducer to a user-perceivable form. The first sensor may be configured to produce the first sensor signal in response to the first sensor sensing displacement of the headset during positioning of the headset relative to the clinician's head. The output device may comprise a user interface that provides user-perceivable output indicative of a plurality of a power status, a transducer signal strength, wired or wireless communication link status, and an operational status of the biosensor.

In some embodiments, methods of the invention involve receiving first and second sensor signals, and discriminating between intended use and nonuse of the biosensor by the clinician based on a state of the first and second sensor signals and using conditional power management logic. Power supplied to biosensor components is controlled based on the state of the first and second sensor signals.

Controlling power supplied to biosensor components may involve controlling application and removal of power respectively to and from biosensor components based on the state of the first and second sensor signals. Controlling power may involve transitioning from a low power mode to an operational power mode in response to the state of a predetermined one of the first and second sensor signals indicating intended use of the biosensor by the clinician. Controlling power may involve transitioning from a low power mode to an operational power mode in response to the state of the first and second sensor signals indicating intended use of the biosensor by the clinician.

Discriminating between intended and nonuse of the biosensor by the clinician may be based on a temporal order of occurrence of the first and second sensor signals and/or a time duration between receipt of the first sensor signal relative to the second sensor signal. Methods may involve disabling implementation of some or all of the conditional power management logic in response to a command signal. Methods may involve implementing or modifying biosensor power management in accordance with a predefined power management profile selectable by the clinician, such as implementing or modifying biosensor power management in accordance with an adaptive power management profile based on biosensor power consumption for past usage of the biosensor.

Methods may involve communicatively coupling the output signal to a user interface, and converting the output signal to a user-perceivable form. For example, methods may involve producing user-perceivable output indicative of a plurality of a power status, a transducer signal strength, wired or wireless communication link status, and an operational status of the biosensor.

According to various embodiments, the power management circuitry is integrated as part of a processor of the biosensor. In other embodiments, the power management circuitry defines circuitry distinct from, but coupled to, the processor. In yet other embodiments, power management circuitry may be distributed between the power management circuitry and the processor. Power management functions, such as discriminating between intended use and nonuse of the biosensor by the clinician or determining readiness of the biosensor for immediate or imminent use by the clinician, may be performed by the power management circuitry, the processor, by both of the power management circuitry and the processor, or any combination of these or other components of the biosensor and/or external devices that communicate with the biosensor.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
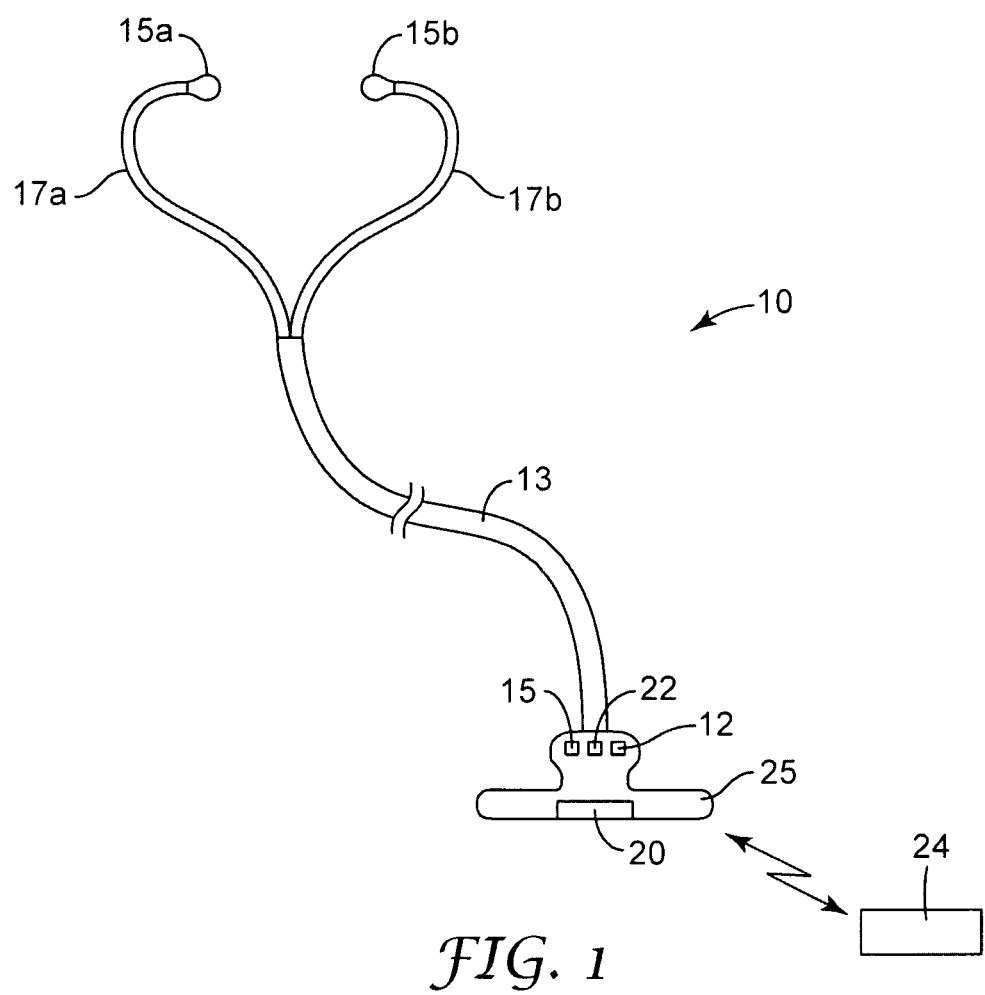
FIG. 1 shows a biosensor in the form of an electronic stethoscope that incorporates power management features in accordance with embodiments of the present invention.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF EMBODIMENTS

In the following description of the illustrated embodiments, reference is made to the accompanying drawings that form a part hereof, and in which are shown by way of illustration, various embodiments in which the invention may be practiced. It is to be understood that the embodiments may be utilized and structural changes may be made without departing from the scope of the present invention.

The present invention relates to power management circuitry and methodologies that may be implemented in electronic devices that are configured to sense of one or more properties associated with matter of biological origin. Representative electronic devices of the present invention include those that are sensitive to sounds and/or other manifestations of energy produced by, or resulting from interaction with, matter of biological origin. Embodiments of the present invention may provide for sensing of one or more of audible sounds, inaudible sounds (e.g., ultrasound or sub-audio sounds), or other acoustic signals or electrical parameters produced by, or resulting from interaction with, matter of biological origin. Embodiments of the present invention may provide for sensing of one of a flow or volume of a fluid, a biopotential, or a structural or compositional property of the human body.

Embodiments of the present invention are directed to power management circuitry and methodologies that may be implemented in a hand-held or portable biosensor, such as an electronic stethoscope. Embodiments of a biosensor of the present invention may incorporate a control system which provides advanced power and operating mode management within a highly interactive medical environment. The control system may be configured to respond to both the actions of the biosensor user (e.g., a clinician) and/or a subject of biosensing (e.g., a patient), and may also respond to communications received from other electronic devices within a medical environment.

Currently marketed electronic stethoscopes, for example, require the clinician to manually turn the unit on. A disadvantage of this 'manual on' system is that the clinician needs to temporarily focus on the stethoscope to locate and then activate the on-off function. A control methodology of the present invention provides means to automatically turn on the electronic stethoscope in anticipation of need, thereby allowing the clinician to focus his or her efforts on patient care rather than taking critical time to activate the stethoscope. A control methodology of the present invention may further provide a visual indication as to the power status of the stethoscope (e.g., confirming ON status) and the current mode of operation (e.g., bell or diaphragm filter), allowing for quick review/adjustment for sounds the clinician is focusing on.

A control system that implements a power management methodology of the present invention may be configured to automatically activate sensors in an electronic stethoscope as well as provide a means to visually communicate the mode of operation and other information to a clinician. For example, a power management methodology of the present invention allows a clinician to activate power circuitry of an electronic stethoscope (e.g., automatic power on/off) without changing the standard workflow that the clinician has developed over many years of using traditional mechanical stethoscopes.

As is well understood, mechanical stethoscopes are always "on," as by definition they do not contain electronics and therefore there is no concern for battery drain or user inconvenience of manual power activation mechanisms (e.g., an ON switch). Clinicians simply place mechanical stethoscope ear tips in their ear canals with the expectation of immediately being able to hear body sounds. A power management approach of the present invention allows for immediate powering-up of circuitry within the electronic stethoscope, thereby simulating an "always on" status of the stethoscope as perceived by the clinician, while conserving battery life.

In general, designs that minimize battery drain during low-activity or "sleep" modes of the stethoscope circuitry are generally preferred. At one extreme, some designs may effectively supplement battery power with energy supplied by the user or the environment. For example, a photovoltaic cell could be exposed to ambient light by separation of the stethoscope's ear tubes, the output voltage of which can be used to activate circuitry which gates the main battery power. Similarly, the act of wearing the stethoscope could mechanically stretch or deform a piece of piezoelectric material, resulting in an output voltage that triggers a mode change in the stethoscope circuitry.

In some embodiments, power management approach of the present invention may provide for activation of power circuitry and other circuitry of a patient-external device that communicates with the electronic stethoscope, such as a PDA, PC or other patient-external device. For example, initiation of the electronic stethoscope's automatic power-on procedure may include generation of a command that causes the patient-external device to power-up, such as from a sleep mode. The command generated by the electronic stethoscope may also initiate a software routine in the patient-external device that configures the external device to operate cooperatively with the electronic stethoscope, such as by launching application software designed to facilitate communication and/or interaction with the electronic stethoscope.

Alternatively, the external device may modify the automatic power-on procedure utilized by the electronic stethoscope. The external device may also command the stethoscope to power-up, such as from a sleep mode.

A control system of the present invention may provide advanced operating mode management in addition to power management. For example, incorporating a perceptible indication of the electronic stethoscope's operating status, such as by use of one or more flashing LEDs and/or an indication on an LCD, OLED, or other type of display, can further provide the clinician valuable information. Information that can be conveyed to the clinician by one or more LEDs or other visual indicators (e.g., on an LCD or OLED display) may include the power status of the stethoscope (e.g., an ON indication after automatic power-on activation) and the filter mode currently being used. For example, illumination of an LED or transition from one color to another (e.g., from red to green) may indicate automatic activation of power circuitry of the stethoscope. Flashing of the LED in a particular manner may indicate the particular filter mode selected or currently being used. A textual or graphic indication of stethoscope power state may be indicated on an LCD, OLED or other type of display.

Moreover, controlling the rate of the flashes (e.g., once per 6 or 10 seconds) may allow the clinician the ability to use the flashes on the stethoscope, instead of a second hand on a watch, when determining heart rates. For example, the clinician may count heart rates between flashes and then multiply the results by 6 or 10 depending on the selected or programmed flash rate. Multiple LEDs may be used to convey different information to the clinician. Alternatively, a single LED may be used to convey multiple types of information to the clinician. One or more LEDs or displays may be situated at a single location of the electronic stethoscope or at multiple locations. Heart rate, signal waveforms, and other information may be displayed on a display of the stethoscope, such as an LCD or OLED display.

In general terms, control circuitry and methodologies of the present invention may be implemented in medical devices that are configured for sensing sounds and/or other manifestations of energy produced by, or resulting from interaction with, matter of biological origin. Many types of medical devices may be implemented in accordance with the present invention, particularly those configured for auscultation, and may be configured to be sensitive to sounds produced by the heart, lungs, vocal cords, or other organs or tissues of the body, for example. Other medical devices that may be implemented in accordance with the present invention include devices configured to sense other properties of the human body, such as flow or volume of a fluid (e.g., a body fluid or air during inspiration/expiration), a biopotential (e.g., action potentials, such as cardiac, nervous system, muscle, and glandular action potentials), and a structural or compositional property of the human body (e.g., property of bone, such as bone density, soft tissue, organs, blood, blood gasses and blood chemistry). By way of example, a device of the present invention is preferably implemented as an electronic stethoscope, but may also be implemented in a headset or other externally worn or coupled apparatus or instrument that senses sounds or other physiological indications produced by the body.

According to various embodiments of the present invention, an electronic stethoscope may be implemented to be preferentially sensitive to a range of frequencies associated with human hearing. It is understood, however, that frequencies associated with body sounds below and/or above the auditory range of frequencies may also be sensed by an electronic stethoscope of the present invention. For example, an electronic stethoscope of the present invention may incorporate one or more sensors implemented to sense body sounds that have frequencies ranging between just above DC and about 25 kHz.

An electronic stethoscope of the present invention may incorporate one or more sensors configured to produce an audible output that falls within the auditory frequency range, and may also produce an electrical or optical sensor that includes content above and/or below the auditory frequency range. The electronic stethoscope may include signal processing circuitry and software that performs frequency-shifting or other signal processing to utilize signals developed by sensors whose range is beyond that of the human auditory system. Such circuitry and software may also be configured to produce data of analytical value.

Turning now to FIG. 1, there is shown a biosensor in the form of an electronic stethoscope that incorporates a power management methodology of the present invention. The electronic stethoscope 10 is configured to include a number of components, such as a pair of ear tips 15a, 15b, ear tubes 17a, 17b, and a main tube 13. The main tube 13 is coupled to a main housing or chestpiece 25, within which at least one sensor 20 is disposed. Sensor 20 is configured to sense sounds produced by matter of biological origin, such as sounds produced by the heart, lungs, vocal cords, or other organs or tissues of the body. Other components that may be disposed in the main housing 25 include a power source, signal processing circuitry, and a communications device.

The signal processing circuitry of the electronic stethoscope 10 may be configured to perform a variety of functions, ranging from simple to complex. For example, the signal processing circuitry may be configured to perform relatively sophisticated analysis of bioacoustic signals received from the sensor 20, such as body sound profile matching. The signal processing circuitry may perform various forms of statistical analysis on signals produced by the sensor 20. In such configurations, the signal processing circuitry may include a digital signal processor (DSP). Alternatively, or in addition, an external system 24 may perform all or some of such signal processing and analyses. The external system 24 may include a display, sound system, printer, network interface, and communications interface configured to establish uni- or bi-directional communication with the communications device disposed in the main housing 25 of the stethoscope 10.

According to one system implementation, the electronic stethoscope 10 may be configured to communicate with a portable, wireless external system 24, such as a PDA, laptop or tablet PC, or other wireless device. The wireless external system 24 may further be configured to communicate with a local or remote server system, such as a networked server system. Information acquired by the electronic stethoscope 10 during auscultation, for example, may be transmitted to the wireless external system 24. The wireless external system 24 may process the information to provide various output data, such as a visual, graphical and/or audible representation of the information (e.g., heart rate indication, S1-S4 heart sounds), and/or diagnostic information regarding anomalous cardiac, lung, or other organ function (e.g., cardiac murmurs such as those resulting from valve regurgitation or stenosis, breathing disorders such pneumonia or pulmonary edema) or other organ pathology.

Analyses requiring significant data or signal processing may be performed by the wireless external system 24, rather than by the processor of the electronic stethoscope 10, or by a remote server. According to one implementation, processing of information acquired by the electronic stethoscope 10 is performed by multiple system elements based on processing resources of each of the system elements. For example, the processor of the electronic stethoscope 10 may be configured to perform rudimentary functions, such as signal filtering and waveform generation that may involve sampling and/or analog-to-digital conversion, and user feedback generation, such as illumination of indicators (e.g., LEDs or display text/graphics) or production of audible output. A PDA or other external system 24 may be configured to perform more advanced functions, such as identification of cardiac murmurs or arrhythmias using various techniques, such as template-based morphological analysis, rate or timing analysis, frequency spectrum analysis, or pattern recognition analysis, among others.

The communications device of the electronic stethoscope 10 may be implemented to establish a conventional radio frequency (RF) link that is traditionally used to effect communications between local and remote systems as is known in the art. The communication link between communications device and external system 24 may be implemented using a short-range wireless communication interface, such as an interface conforming to a known communications standard, such as a Bluetooth standard, IEEE 802 standards (e.g., IEEE 802.11), a ZigBee or similar specification, such as those based on the IEEE 802.15.4 standard, or other public or proprietary wireless protocol. Wireless communication may be implemented in manners that utilize one or several of the following energy forms: electromagnetic radiation, optical (including near infrared), and acoustic (including high frequency beyond average hearing limit).

It is understood that the electronic stethoscope 10 may be implemented to include a hardwire connector instead of, or in addition to, a wireless communications capability. In such a configuration, a conductor (electrical or optical) may be connected between the hardwire connector or port of the electronic stethoscope 10 and an appropriate connector of a patient-external system 24. The hardwire connection port of the electronic stethoscope 10, and any necessary interface circuitry, may be configured to communicate information in accordance with a variety of protocols, such as FireWire™ (IEEE 1394), USB, or other communications protocol.

The sensor 20 of an electronic stethoscope 10 of the present invention preferably incorporates a transducer 20 that is configured to modulate or generate an electrical signal in response to deformation of the transducer. Suitable transducers are those that incorporate piezoelectric material (organic and/or inorganic piezoelectric material) such as piezoelectric film, piezoresistive material, strain gauges, capacitive or inductive elements, a linear variable differential transformer, and other materials or elements that modulate or generate an electrical signal in response to deformation. The transducer 20 may be planar or non-planar, such as in the case of a curved or corrugated configuration. Suitable piezo materials may include polymer films, polymer foams, ceramic, composite materials or combinations thereof. The transducer 20 may incorporate arrays of transducers of the same or different transducer type and/or different transducer materials, all of which may be connected in series, individually, or in a multi-layered structure. Suitable transducers that incorporate plural sensing elements having differing characteristics and/or sensors with tailorable sensing characteristics are disclosed in commonly owned U.S. Published Patent Application Nos. 2007/0113649 and 2007/0113654, each of which is incorporated herein by reference.

Transducer 20 may be implemented using technologies other than those that employ electromagnetic energy or piezo materials. For example, the sound to be transduced may move a cantilever that has a highly reflective surface, and a laser or optical beam of light shining on this surface may be modulated. The intensity or other property of the modulated light may be received by a photodetector that outputs an electrical signal for analysis.

As discussed previously, one or more LEDs or displays may be used to convey information to the clinician. One or more LEDs and/or displays may be situated at a single location of the electronic stethoscope or at multiple locations. For example, multiple LEDs 12, 15, and 22 are shown mounted on the housing (i.e., chestpiece), it being understood that embodiments of the present invention may be implemented using a signal LED or other type of visual indicator or display.

A power management methodology of the present invention may be implemented in an electronic stethoscope in a variety of ways. For example, activation of power-on circuitry of the electronic stethoscope can be initiated based on headset operation. Activation of power-on circuitry of the electronic stethoscope can be initiated based on sensing contact or proximity between the chestpiece and the clinician's hand and/or between the chestpiece and the patient's skin or clothing. A conductive surface or pressure applied to and removed from the surface or edges of the chestpiece may be used to activate and deactivate power supply circuitry of the stethoscope. A change in temperature caused by handling the stethoscope (e.g., clinician touching and/or patient contact with the chestpiece) may be sensed and used to activate and deactivate power supply circuitry of the stethoscope. Powering on and off the stethoscope may be controlled via measuring changes in impedance, capacitance, resistance or other electrical parameter, such as when the stethoscope ear tips are placed into and removed from ear canals. Powering on and off the stethoscope may be controlled by a mechanical, electrical, magnetic or optical switch or sensor, or a combination of such switches and sensors.

According to embodiments of the present invention, activation of power-on circuitry of the electronic stethoscope may be initiated based on headset operation. The headset is understood to include the ear tubes and ear tips of a stethoscope. When the headset is opened, such as by pulling the headset tubes/ear tips apart, the power-on circuitry of the electronic stethoscope is activated so that the stethoscope is ready for immediate use by a clinician. It is noted that pulling headset tubes apart is the "normal procedure" that clinicians use when they are planning to auscultate a patient using the stethoscope. In addition to inclusion of power-on circuitry, an electronic stethoscope of the present invention may further include power-off circuitry. For example, when the headset is removed from clinician's ears, thereby allowing the headset to return to its closed or relaxed configuration, the power-off circuitry senses this action and deactivates power supplied to the stethoscope, preferably after a predetermined period of time.

Figure 2A:
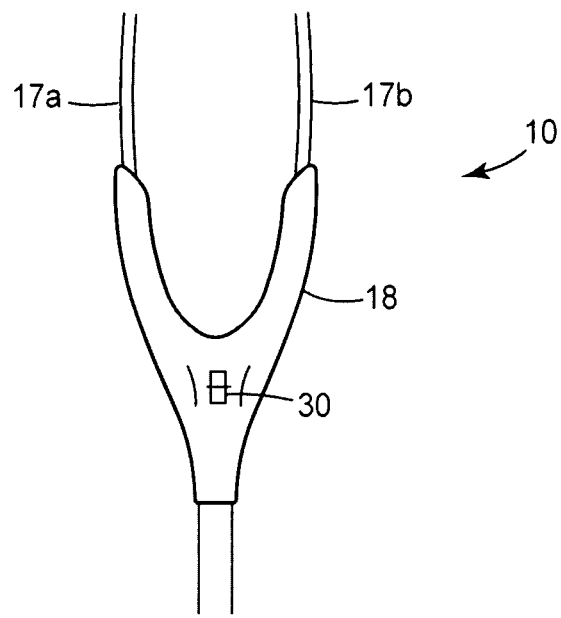
FIGS. 2A and 2B illustrate a mechanism for sensing impending need for stethoscope usage by a clinician in accordance with embodiments of the present invention.
Figure 2B:
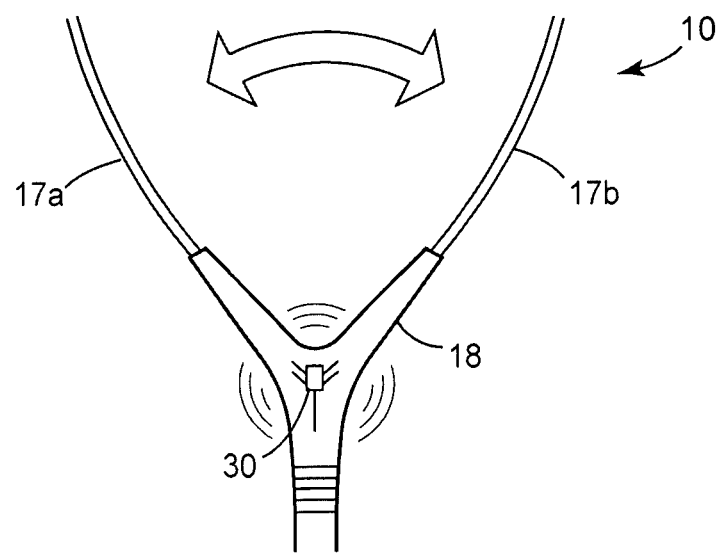

FIGS. 2A and 2B illustrate a mechanism for sensing impending need for stethoscope usage in accordance with embodiments of the present invention. FIGS. 2A and 2B show ear tubes 17a, 17b coupled to a yoke 18 of electronic stethoscope 10. The ear tubes 17a, 17b shown in FIG. 2A are in their relaxed configuration. FIG. 2B shows ear tubes 17a, 17b being forcibly displaced from one another, which would occur when a clinician situates the electronic stethoscope 10 on his or her person for imminent use.

A sensor 30 is shown disposed in or on the yoke 18 of the electronic stethoscope 10. Ear tubes 17a, 17b are coupled to the yoke 18. The sensor 30, according to this illustrative embodiment, is configured to sense mechanical displacement or force of displacement of ear tube 17a relative to ear tube 17b. In one configuration, the yoke 18 includes a compliant portion at which the sensor 30 is situated. As best shown in FIG. 2B, forcible displacement of ear tube 17a relative to ear tube 17b results in deformation of the yoke 18, such deformation being sensed by the sensor 30. In other configurations, the yoke need not include a compliant portion, and the sensor 30 may be configured to sense ear tube displacement directly. For example, strain, deflection, or torsion, or other indication of mechanical distortion or displacement of the ear tubes 17a, 17b, for example, may be sensed using appropriate sensors mounted to or proximate the ear tubes 17a, 17b, thus allowing for a yoke 18 that is substantially rigid.

The sensor 30 is preferably calibrated to distinguish between imminent intended use of the electronic stethoscope 10 and spurious movement of the ear tubes 17a, 17b, such as movement indicative of stethoscope transport or other forces not associated with imminent intended use of the electronic stethoscope 10 by a clinician. For example, the sensor 30 may be calibrated to generate an activation signal in response to ear tube displacement or force of displacement exceeding a predetermined threshold. The sensor 30 may be configured to detect ear tube displacement along a single axis (e.g., x-axis as shown in FIG. 2B) or multiple axes (x-, y-, z-axes). For example, the sensor 30 may incorporate multiple force or accelerometer sensors aligned in an orthogonal relationship, from which ear tube displacement relative to each axis may be detected. Thresholds may be established for each axis of movement developed from empirical use data that distinguish between impending clinician usage and spurious movement. It is understood that a multi-axis sensor 30 may be employed elsewhere on the stethoscope.

Figure 3:
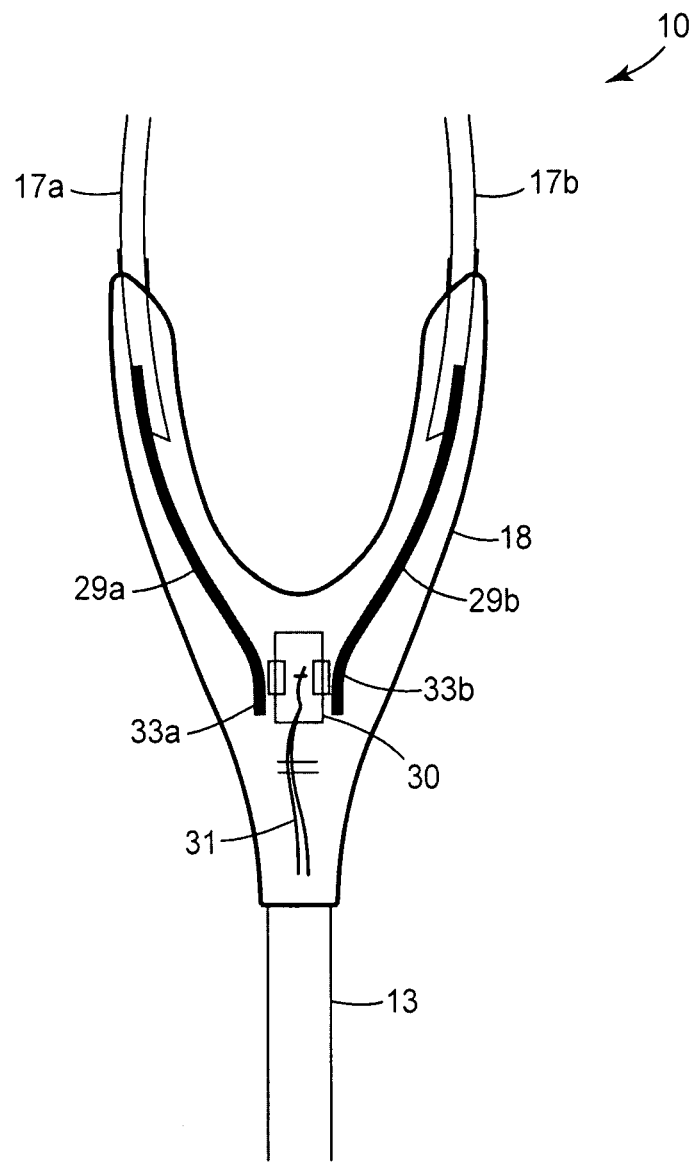
FIG. 3 illustrates a sensor configured for sensing impending clinician usage of an electronic stethoscope in accordance with embodiments of the present invention.

FIG. 3 illustrates a sensor 30 configured for sensing impending clinician usage of an electronic stethoscope in accordance with embodiments of the present invention. The yoke 18 in FIG. 3 is shown to include a sensor 30 mounted proximate two sense members 29a, 29b. The sense members 29a and 29b are mechanically coupled to ear tubes 17a and 17b, respectively. Displacement and forces of displacement applied to ear tubes 17a and 17b are transmitted to sense members 29a and 29b, causing relative movement between sense member ends 33a and 33b and the sensor 30. A sufficient degree of displacement of the ear tubes 17a, 17b from one another as sensed by the sensor 30 results in generation of an activation signal by the sensor 30. The activation signal is transmitted to power control circuitry of the electronic stethoscope 10, preferably housed in the chestpiece, by conductor(s) 31 via main tube 13.

In this embodiment, sense member ends 33a and 33b are spaced apart from the sensor 30 when in a relaxed state. Changes in gap spacing between the sense member ends 33a and 33b and the sensor 30 (and contact therebetween according to some embodiments) may be sensed in a variety of ways. According to one embodiment, the sensor 30 may be configured to include a capacitive sensor that senses changes in gap spacing between the sense member ends 33a and 33b and the sensor 30.

In another embodiment, the sensor 30 is configured to sense contact between the sense member ends 33a and 33b and the sensor 30. Such contact can be sensed as a change in an electrical or mechanical parameter of the sensor 30. For example, the sensor 30 may be configured to include an electrically conductive element, such that contact between the sense member ends 33a and 33b and the sensor 30 closes an electric circuit that includes the electrically conductive element. In other embodiments, an optical element may optionally be used in the sensor 30 to detect displacement and/or contact between the sense member ends 33a and 33b and the sensor 30. In further embodiments, a pressure sensor may be incorporated in the sensor 30 for sensing contact between the sense member ends 33a and 33b and the sensor 30.

Figure 4A:
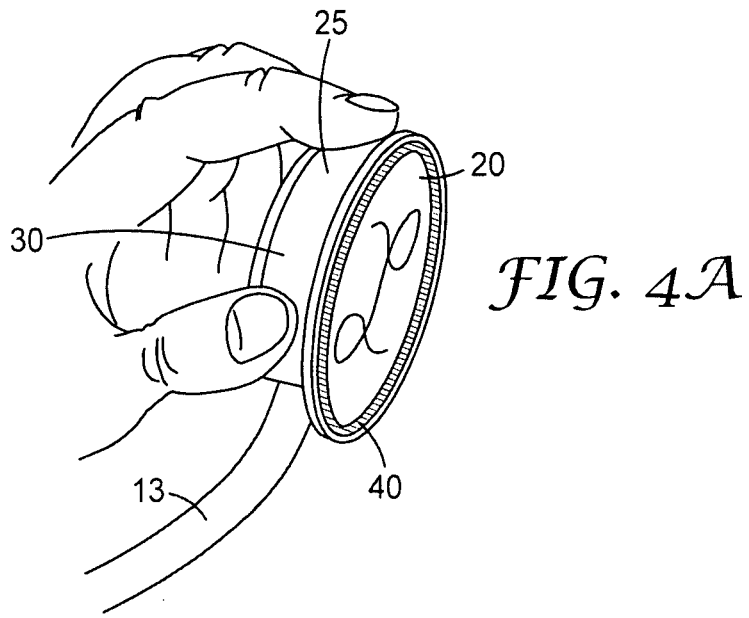
FIGS. 4A-4C illustrate power management control features configured to sense imminent clinician need for electronic stethoscope usage in accordance with embodiments of the present invention.
Figure 4B:
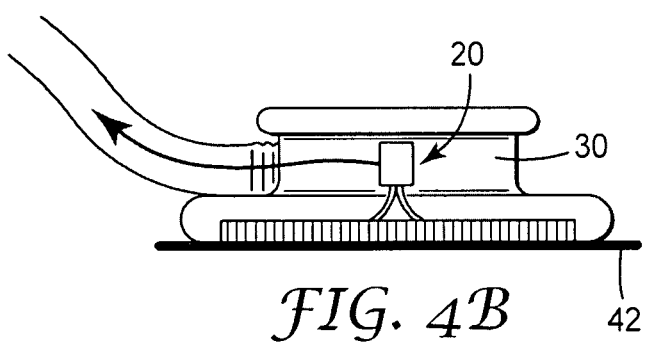
Figure 4C:
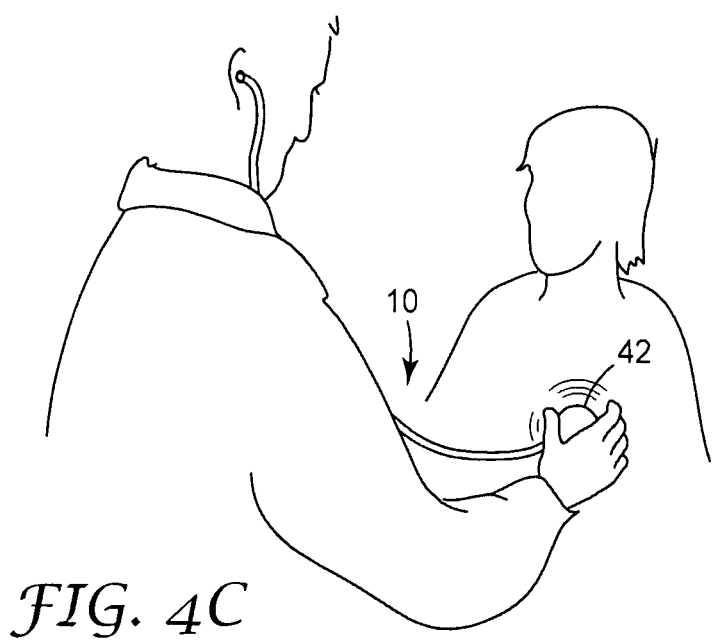

FIGS. 4A-4C illustrate power management control circuitry configured to sense imminent clinician need for stethoscope usage in accordance with other embodiments of the present invention. FIGS. 4A-4C illustrate provision of sensor 30 at the chestpiece. In one configuration, the sensor 30 is configured to sense contact between the clinician's hand or fingers and the housing 25 of the chestpiece. In another configuration, the sensor 30 is configured to sense contact between the diaphragm 20 of the chestpiece and the patient's skin or outer clothing 42. For example, a ring sensor 40, such as a conductive, capacitive, or pressure sensing ring, may be incorporated on the diaphragm surface 20. The ring sensor 40 may be configured to sense proximity of the chestpiece to a body surface or clothing of the patient, such that contact is not necessarily required as an indicator of imminent intention of stethoscope usage. In a further configuration, the sensor 30 may sense both clinician/housing contact and diaphragm/patient contact, such that activation of stethoscope power circuitry is based on the state of sensing multiple conditions.

For example, sensing of both clinician/housing contact (or proximity) and diaphragm/patient contact (or proximity) may result in activation of stethoscope power circuitry. In one configuration, sensing of clinician/housing contact (or proximity) or diaphragm/patient contact (or proximity) may result in activation of some components of the stethoscope, with the remaining components (e.g., more power consuming components) being activated in response to sensing both clinician/housing contact/proximity and diaphragm/patient contact/proximity, thereby confirming imminent clinician need for usage of the stethoscope.

Contact or proximity between the clinician's hand/fingers and the housing 25 or between the diaphragm 20 of the chestpiece and the patient's skin or outer clothing may be sensed in a variety of ways. For example, pressure applied to the patient contact surface of the chestpiece, such as the diaphragm surface 20, can be used to activate and deactivate stethoscope circuitry. Removal of pressure could then be sensed to deactivate stethoscope power. This approach may also be used to determine uniform contact between the diaphragm 20 and patient for best auscultation by use of multiple contact points. Capacitance may be used to detect proximity between the housing 25 and the clinician and/or patient, and to activate and deactivate stethoscope circuitry.

Figure 5A:
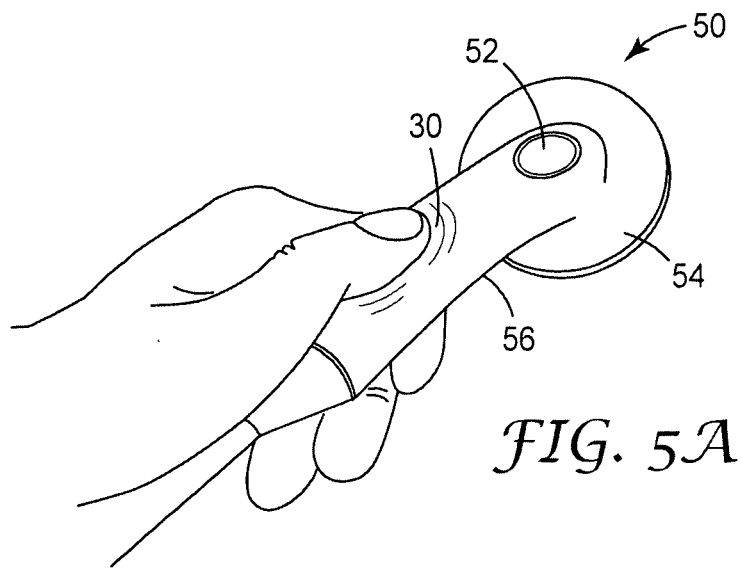
FIGS. 5A-5C illustrate power management control features configured to sense imminent clinician need for electronic stethoscope usage in accordance with other embodiments of the present invention.
Figure 5B:
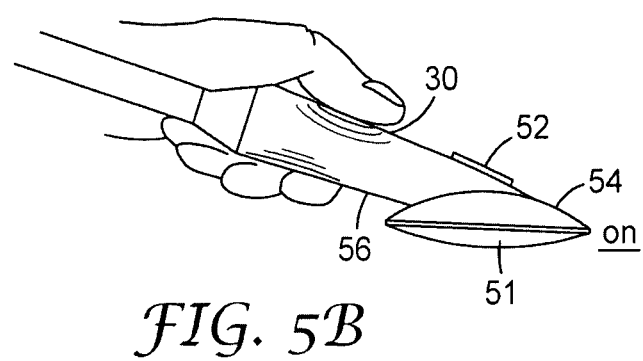
Figure 5C:
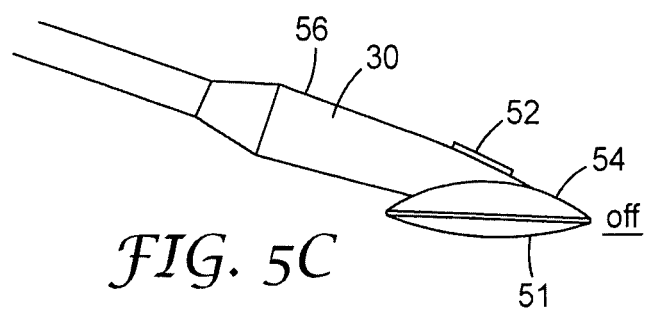

FIGS. 5A-5C illustrate another embodiment of an electronic stethoscope that employs temperature sensing as a mechanism for activating and deactivating power supply circuitry of the stethoscope. The stethoscope 50 shown in FIGS. 5A-5C incorporates a sensor 30 that is configured to sense temperature. FIGS. 5A and 5B depict activation of stethoscope power supply circuitry in response to the sensor 30 sensing a temperature increase relative to ambient at the handle 56 resulting from the clinician picking up the stethoscope 50. FIG. 5C illustrates deactivation of stethoscope power supply circuitry in response to the sensor 30 sensing a temperature decrease at the handle relative to the temperature reached during clinician usage or in relation to a threshold established relative to ambient temperature.

Useful temperature sensors 30 include those that incorporate thermistors, infrared (IR) photodiodes, or temperature sensitive films or materials, for example. Various temperature sensitive devices or materials may be used to sense and transduce temperature and changes in temperature at one or more locations of the stethoscope 50 that are typically contacted by the clinician or patient. For example, one or both of the handle 56 and diaphragm or patient-contacting portion 51 of the chestpiece 54 may incorporate a temperature sensor 30. A reference ambient temperature may be obtained using a temperature sensor situated at a location of the stethoscope where contact with the user or patient is unlikely.

FIG. 5A also shows a device 52 that may be configured as a mode switch, a display or a combination of these features. For example, a multi-mode switch 52 may be depressible by the clinician to select and de-select various functions, including filter modes, gain modes, and volume control. The device 52 may alternatively, or additionally, include a display, such as an LCD or OLED display for displaying various information, such as heart rate, battery status, and mode status, for example.

FIGS. 6-12 illustrate several embodiments of power management and control circuitry that may be implemented in an electronic stethoscope in accordance with the present invention. Conventional approaches for stethoscope power management include the use of an electrical switch within the binaural assembly, such as described in U.S. Pat. No. 6,005,951, which is hereby incorporated herein by reference. Other approaches for stethoscope power management include timer circuits that automatically shut off stethoscope power after a pre-determined time interval. These approaches provide limited flexibility in responding to user workflows and do not support automatic interaction with wireless medical systems and networks. Such conventional approaches typically reflect an "all or nothing" approach to power management, rather than a graded approach that more comprehensively monitors user actions or the general operating environment of the electronic stethoscope.

With reference to FIGS. 6-12, electronic stethoscopes of the present invention, in general, include a number of components, including one or more sources of electrical power as well as a variety of sensors, signal processing elements, control logic, memory elements, and communication links. The sensor or sensors that sense imminent clinician need for stethoscope usage may be passive (i.e., requiring a supply of power for its operation) or active (i.e., generates its own electrical signal by some mechanism, such as piezoelectric, electromotive, or other means).

Figure 6:
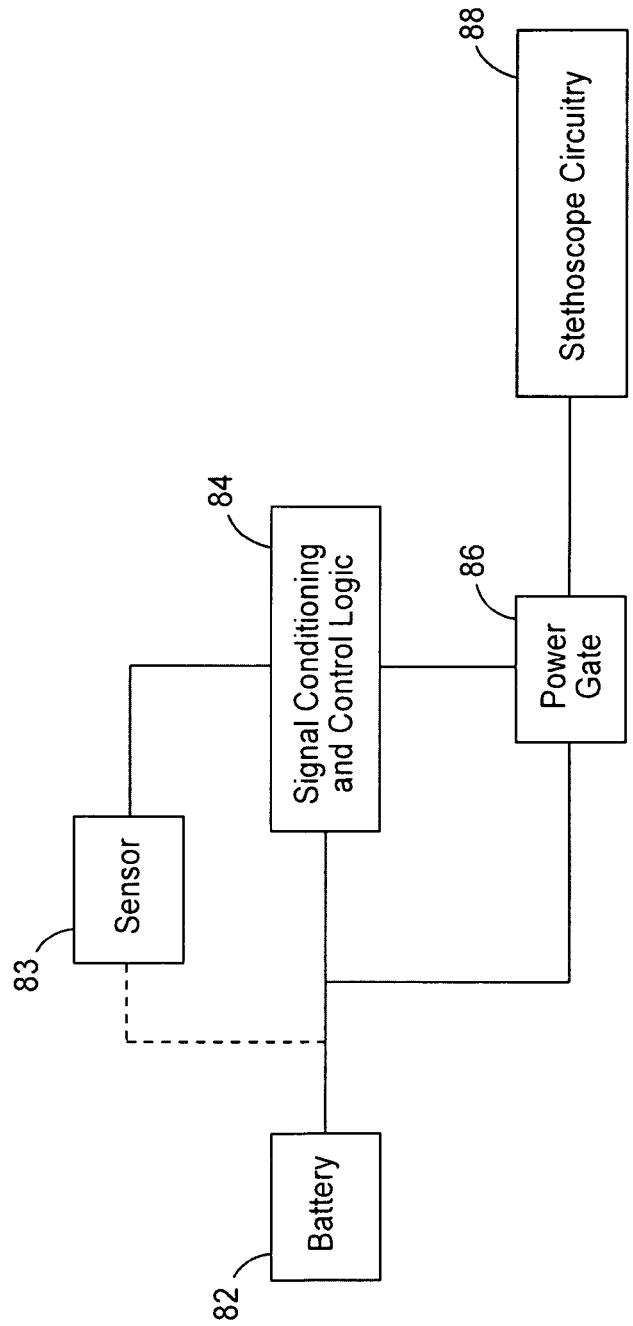
FIGS. 6-12 illustrate several configurations of power management and control circuitry that may be implemented in an electronic biosensor in accordance with embodiments of the present invention.

The embodiment of power management circuitry illustrated in FIG. 6 includes a battery 82 coupled to a power gate 86 and signal conditioning and control logic 84. A sensor 83 is coupled to the logic unit 84. The sensor 83 may be passive or active. It is noted that logic unit 84 preferably draws minimal power from the battery 82 during non-use of the stethoscope. Various known sleep mode techniques may be implemented by which minimal power is required by the logic unit 84 to detect activation of sensor 83. The sleep mode circuitry may generate a wake-up or activation signal to effect powering-up of the stethoscope circuitry 88 to facilitate immediate use of the stethoscope by the clinician.

As is shown in FIG. 6, the logic unit 84 controls power gate 86 in response to the wake-up or activation signal to facilitate supplying of power to the stethoscope circuitry 88 by the battery 82. The sensor 83 may also sense non-use of the stethoscope, as previously discussed, in which case the logic unit 84 deactivates the power gate 86 to remove power from the stethoscope circuitry 88 and returns to sleep mode.

The sensor 83 may be implemented in a wide variety of ways as discussed previously and elsewhere herein. The sensor 83 may be configured to sense acoustic emissions from the human body or other property of the human body, such as flow or volume of a fluid (e.g., a body fluid or air during inspiration/expiration), a biopotential (e.g., potentials generated during the excitation of nerve and muscle tissue), or a structural or compositional property of the human body (e.g., property of bone, such as bone density, soft tissue, organs, blood, blood gasses and blood chemistry). A non-exhaustive, non-limiting listing of useful sensors 83 include the following: positional, configurational, or orientation sensors; force, stress, or pressure sensors (e.g., accelerometer, strain gauge); thermal sensors (e.g., IR photodiodes, thermistors); optical sensors (e.g., sensor that use reflectors/shutters, and/or an optical circuit in the binaurals); conductive sensors (e.g., mechanically-switched electrical contacts, magnetic-reed switch, film resistor sensors); acoustic (sound threshold sensors, sound discrimination filters, voice recognition sensors); magnetic sensor (e.g.,. Hall-effect sensors); and motion sensors (e.g., single or multiple-axis acceleration, such as a MEMS accelerometer or gyroscope).

Figure 7:
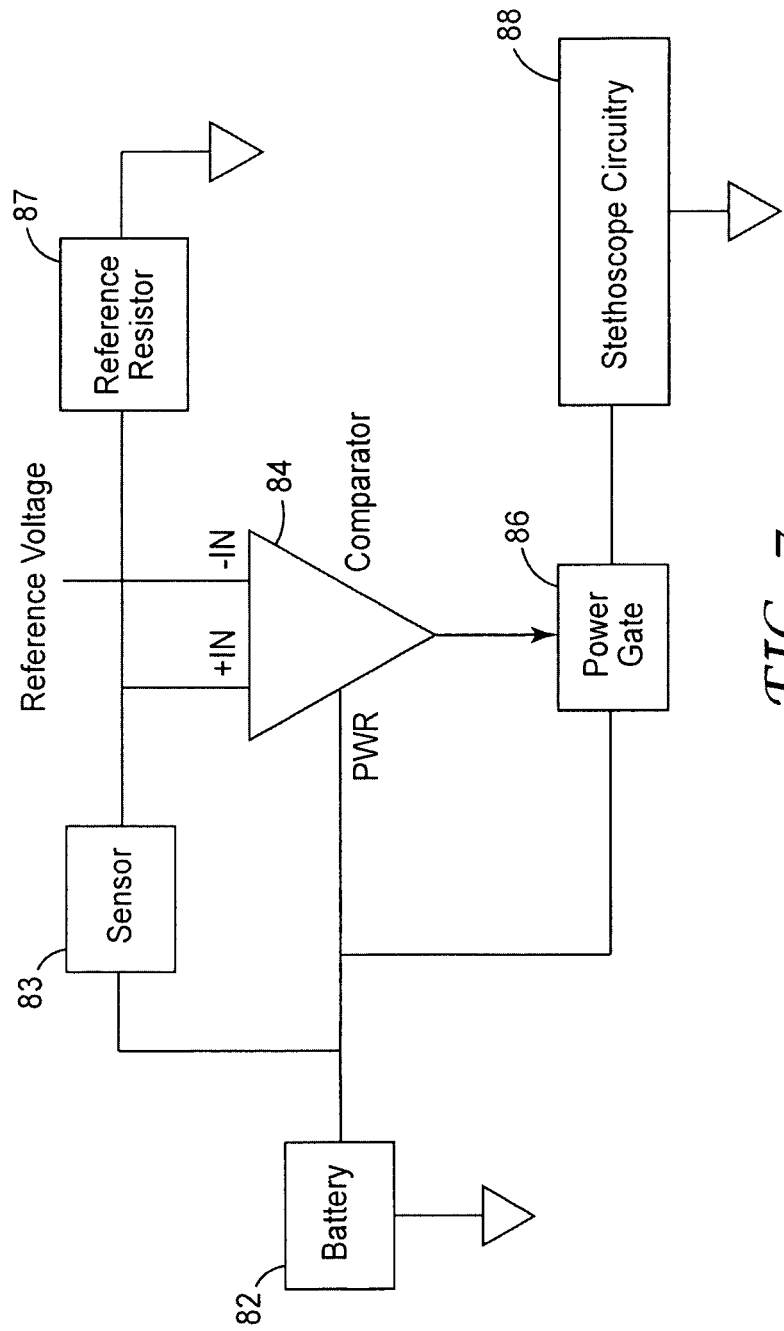
Figure 8:
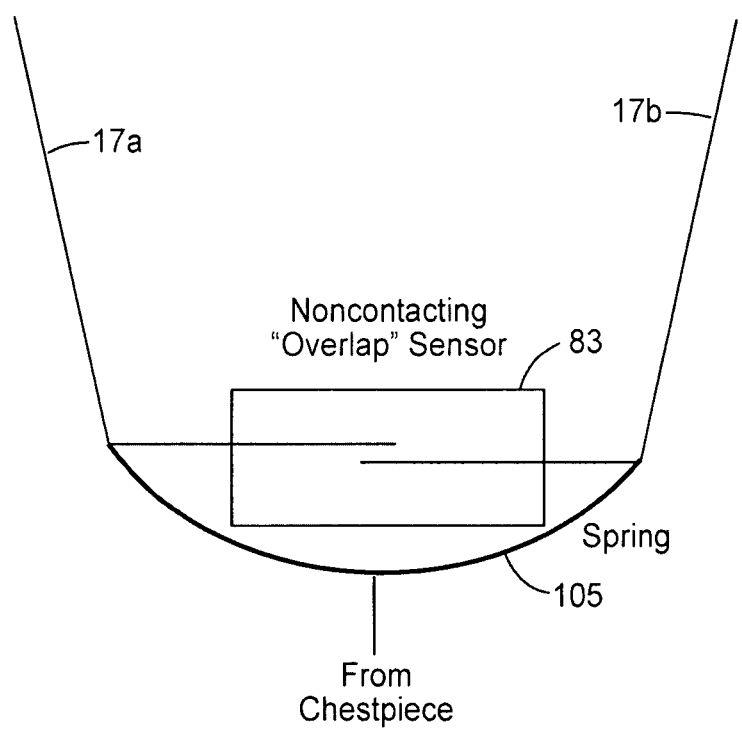

FIG. 7 is a block diagram showing various components of power management circuitry that may be implemented in an electronic stethoscope in accordance with embodiments of the present invention. FIG. 7 illustrates a circuit that includes a sensor 83 mounted on the headset of the stethoscope so as to be sensitive to ear tube displacement. In one arrangement, as best shown in FIG. 8, the sensor 83 may be mounted on a binaural spring arrangement 105. Respective ends of the spring arrangement 105 are mechanically coupled to ear tubes 17a and 17b, respectively.

The spring 105 is configured to expand and contract in response to forces applied to ear tubes 17a and 17b. The sensor 83 shown in FIG. 8 is configured as a non-contacting sensor, such as a non-contacting overlap sensor, where the degree of overlap increases as the spring 105 flexes and decreases as the spring 105 relaxes.

According to one implementation, and as best shown in FIG. 7, the output of a voltage divider or bridge including a reference resistor 87 and a resistive sensor 83 is presented to a micro-power comparator 84. When the output of the bridge exceeds a reference voltage level, a power gate 86 is activated and power is applied to stethoscope circuitry 88 from the battery 82. The resistive sensor 83 can be implemented as a film resistor applied directly to spring 105.

It is understood that the non-contacting sensor arrangement 83 shown in FIG. 8 may be implemented using a wide variety of sensors and sensing techniques, such as those described herein, and that incorporation of a film resistor represents but one of such useful sensors. For example, the following non-contacting and/or overlap sensors 83 may be incorporated into the binaural headset assembly depicted in FIG. 8.

In one implementation, a magnet may be mounted on one slide of the non-contacting sensor 83 and a reed switch may be mounted to a second slide or on a stationary mount within the binaural assembly. Movement of the magnet towards the reed switch closes the contacts of the switch, thereby indicating imminent need of stethoscope usage by the clinician.

In another implementation, a capacitance sensor 83 arrangement that includes plates on the non-contacting slides of the sensor 83 is provided. A capacitance is sensed that varies in relation to the amount of sliding plate overlap (or gap separation, depending on the sensor configuration). In a further implementation, sensor 83 may be configured to include permeable material sliding within a coil. A variable inductance may be measured that is related to the extent of binaural displacement. In another implementation, one of the sliders of sensor 83 acts as a shutter on a light path between a light source and a photodetector, or between ambient light and photosensor, such as a photovoltaic cell, photodiode, or photoresistor, for example. In each of these implementations, a change in the sensor signal beyond a threshold indicates purposeful separation of the headset in anticipation of stethoscope usage by the clinician.

Other sensor configurations are contemplated that can be implemented in or are associated with the chestpiece of the electronic stethoscope rather than the headset. It is understood that a combination of sensors in the chestpiece and the headset may be used to sense and/or verify imminent need for stethoscope usage by the clinician. Examples of such sensors include sensors that detect the relative displacement or rotation of a diaphragm assembly with respect to the main structure of the chestpiece. Other useful sensors include sensors that detect the flexion, bending, rotation, or torsion of the stem of the chestpiece relative to the main structure of the chestpiece. Sensors that sense deformation of a structure on the chestpiece, such as areas used by the clinician when gripping the stethoscope, may also be employed. Resistance sensor affected by external conductance such as that presented by the skin of the user when gripping the chestpiece may be employed.

Various other approaches for sensing imminent clinician need for stethoscope usage may be employed, such as sensors that sense a differential change of a parameter associated with human contact or release of contact. Such sensors may be configured to sense a differential change at the wall of the chestpiece due to the presence of a hand gripping the chestpiece. Such differential changes may be temperature, light, current, or voltage change. In one such implementation, a change in chestpiece temperature due to heating by a user's hand may be sensed and compared to a threshold, such as an ambient or other baseline temperature. In such an implementation, a relatively inaccessible surface of chestpiece may be used as a reference temperature location.

Presence of a hand on the chestpiece may be signaled by blockage of ambient light to photosensor mounted on the chestpiece. A near infrared source detector may be used to determine presence of a periodic voltage change derived from plethysmography at the hand holding the chestpiece. In other implementations, sensors may be placed within stethoscope tubing or cabling (if present) between the chestpiece and the headset to distinguish a coiled from an uncoiled state.

Figure 9:
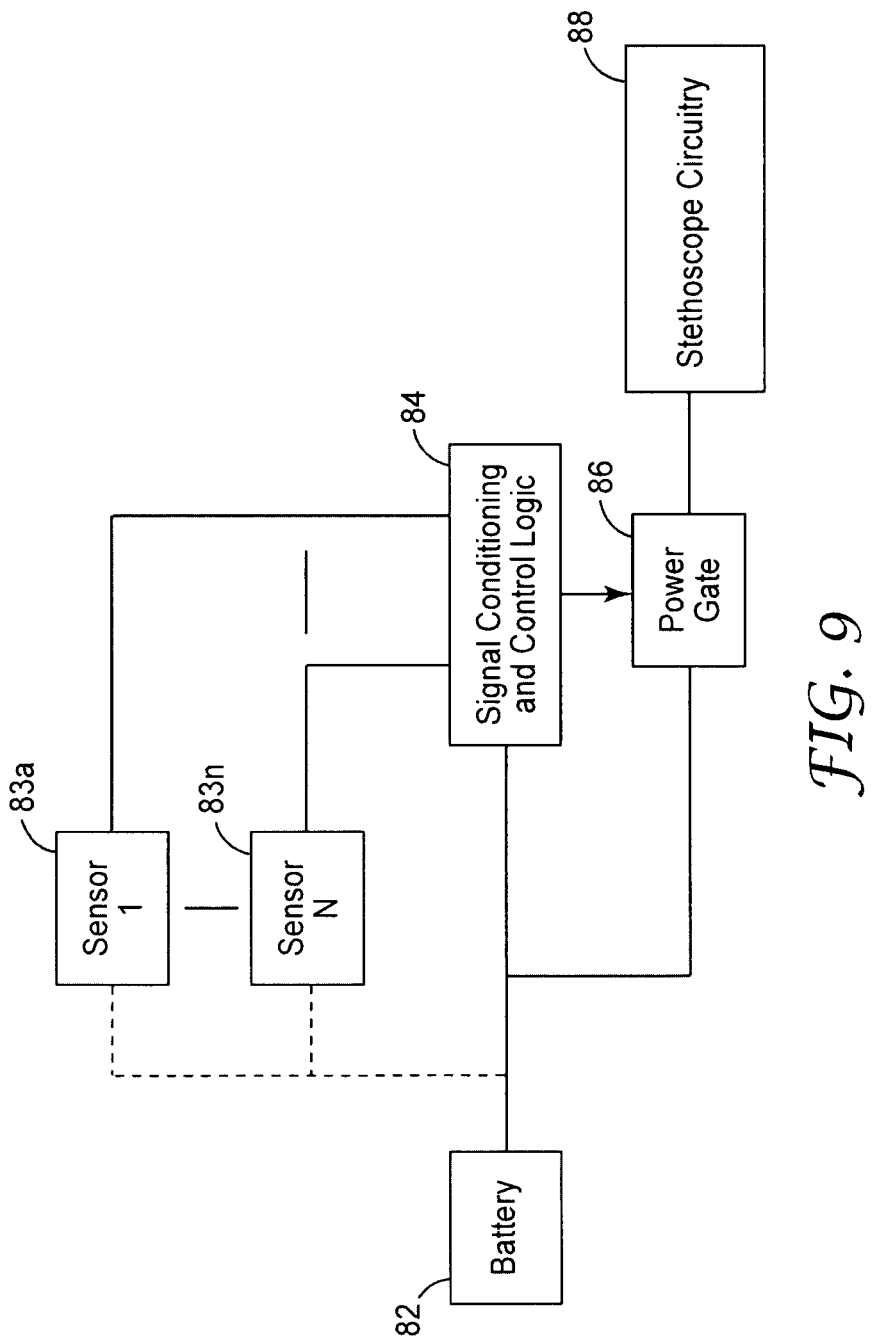

FIG. 9 is a block diagram showing various components of power management circuitry that may be implemented in an electronic stethoscope in accordance with embodiments of the present invention. FIG. 9 illustrates a circuit that includes a multiplicity of sensors 83a-83n. It is understood that a single sensor 83 capable of sensing multiple conditions may also be employed in the context of the embodiment shown in FIG. 9. Use of multiple sensors 83a-83n or multiple sensed conditions using a single sensor provides for conditional activation of stethoscope power circuitry.

According to various embodiments, a "power on" state results from the occurrence of multiple events. FIG. 9 provides a schematic example, in which more than one sensor 83a-83n contributes to the decision process. Alternatively, a single sensor could be used to detect multiple events. In either case, the temporal order in which events occur may also be important.

In one implementation, an acoustic sensor may be provided behind the diaphragm of the chestpiece. The acoustic sensor may be used in combination with a configurational sensor in the headset assembly of a type previously described. In another implementation, a contact pressure sensor may be mounted on the chestpiece diaphragm and used in combination with a conductance sensor (e.g., skin contact sensor) provided on the chestpiece grip. Other combinations of sensors and sensing techniques are contemplated.

The approach of using multiple forms of sensor information may be useful when an event may not always indicate an intention to use the stethoscope. For example, movement of the stethoscope in a lab coat during routine transport could activate an acoustic sensor. Similarly, placement of the binaural assembly around the neck could flex the ear tubes without the ear tips necessarily residing in the ear canals. Many of the examples discussed hereinabove may be used to implement a multiple sensor approach.

According to a further approach, the sensor 83 utilizes a small high frequency current (microampere or less), with the stethoscope constituting one section of the circuit and the clinician (e.g., clinician's two hands) forming a second part of the circuit. The circuit may be completed by allowing the current to flow through various routes that include some part of the clinician's body and some portion of the stethoscope as a necessary part to complete the circuit. Irrespective of the particular sensing scheme that is utilized to detect impending use of the scope and its activation, such schemes should preclude accidental operation, as may happen during transportation in a glove compartment of a car or the pocket of clothing worn by the clinician.

The use of multiple sensors may also enable a user to "personalize" a stethoscope by choosing from a set of options for power-up events. In this fashion, event(s) most consistent with a given workflow or examination procedure could be selected.

Figure 10:
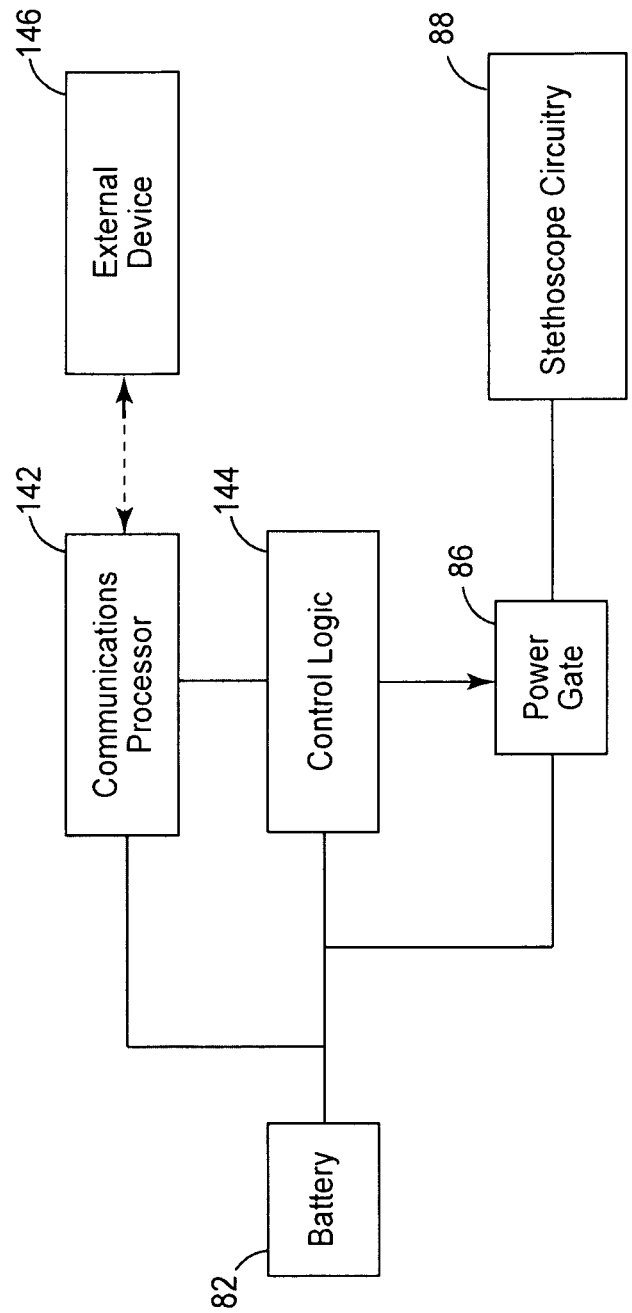

As discussed previously, an electronic stethoscope of the present invention may interact cooperatively with a patient-external system or device. FIG. 10 is a block diagram illustrating one embodiment of an electronic stethoscope of the present invention that communicates with a patient-external system or device. As shown in FIG. 10, a communications processor 142 of the stethoscope receives input from an external device 146. A power management methodology implemented by the control logic unit 144 of the stethoscope may be responsive to the input received from the external device 146. Conversely, a power management methodology implemented by the external device 146 may be responsive to the input received from the control logic unit 144 of the stethoscope.

In some situations, it may be desirable to turn on power to the stethoscope, or change its operating mode, under the command of another device. For example, an event could be generated via an external communications link (e.g., a wireless transponder-initiated event or event over wired interface). For telemedicine applications, for example, an electronic stethoscope of the present invention could be activated from a relay station connected to a remote central console. The stethoscope's operating state, including amplitude and filter settings for example, may also be set by remote command.

In another configuration, a stethoscope system in which a separately powered, wireless headset for the stethoscope initiates the power-on or changes the operating mode of circuitry within the chestpiece. In other words, if the stethoscope has essentially a distributed structure, with independently powered elements, a power-on or operational mode change can be communicated/cascaded across the complete system.

According to further embodiments of the present invention, power management of an electronic stethoscope may be modified responsive to a variable duration of an operating mode change. The duration of an operational mode change could be quite different from the original, initiating event. The duration of the change could be fixed or be adjusted according to user workflow. The sensor could be regularly (and even continuously) interrogated by an adaptive control system.

For example, if inactivity is sensed well before a preset timer interval has elapsed, power could be trimmed or cut off early to minimize battery discharge and thus increase battery life. Similarly, the rate of sensor interrogation could be reduced according to predictive models of stethoscope use based on recent sensor activity.

The pattern of activity noted from sensor configurations described in the examples hereinabove may also be used to change the operating mode of the stethoscope in sequences appropriate to the workflow of a stethoscope user. Also, sensor activity may also change or modulate operational parameters or characteristics of the signal processing circuitry, such as filter responses and amplitude levels. As such, the control system and methodologies of controlling an electronic stethoscope of the present invention may be broadened beyond power management to include other operational elements of the stethoscope.

Figure 11:
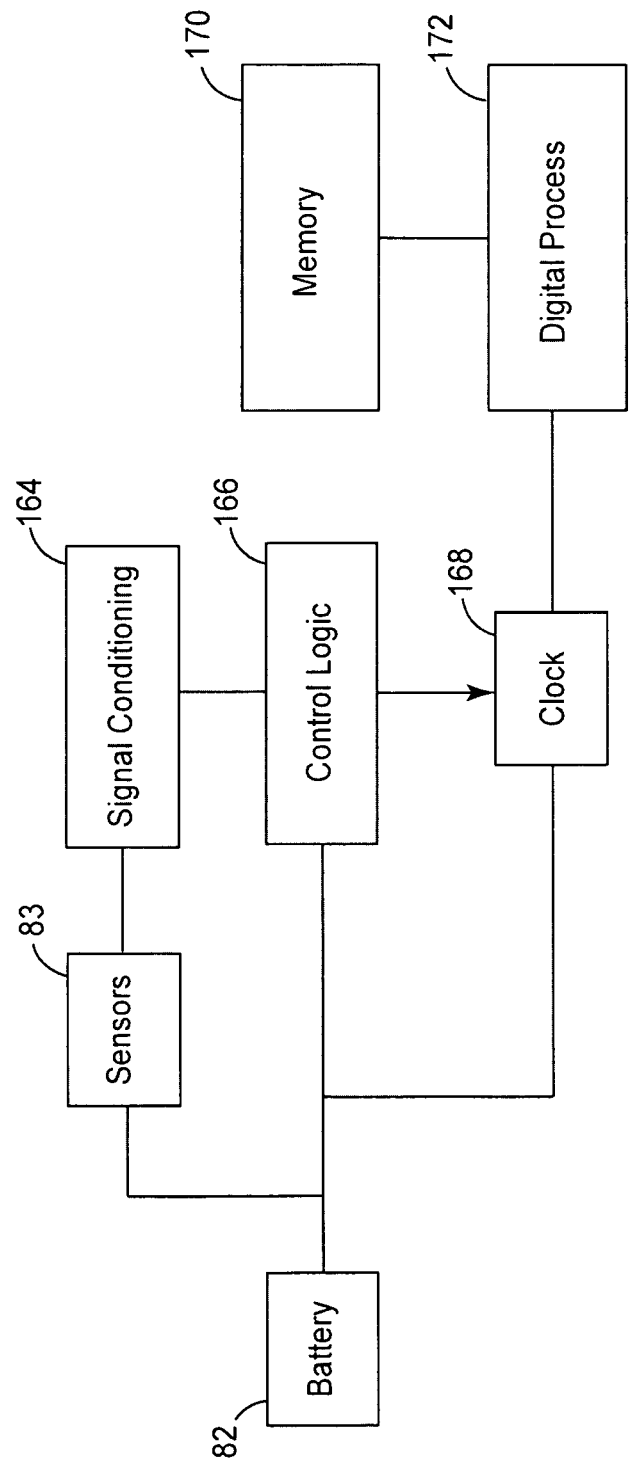

Many electronic circuits today are never powered off completely except for a change in batteries. Instead, such circuits are placed in a low-power "standby" mode, in which the circuit operations are limited in their type or execution speed ("throughput"). FIG. 11 shows a block diagram of circuitry that provides for a standby or sleep mode of stethoscope operation in accordance with embodiments of the present invention. As shown in FIG. 11, signals generated by one or more sensors 83 are communicated to a control logic unit 166, typically after processing by signal conditioning circuitry 164. The sensor signals input to the control logic unit 166 cause the control logic unit 166 to adjust the frequency of a clock 168 that provides clocking pulses for an embedded digital processor 172. Although the processor remains continuously active, it spends most of its time in a low-power operating state. Other circuits of the stethoscope may also be controlled to switch to a low-power operating state when such circuits need not be active, such as memory 170 and portions of the control logic unit 166 and signal conditioning circuitry 164.

Figure 12:
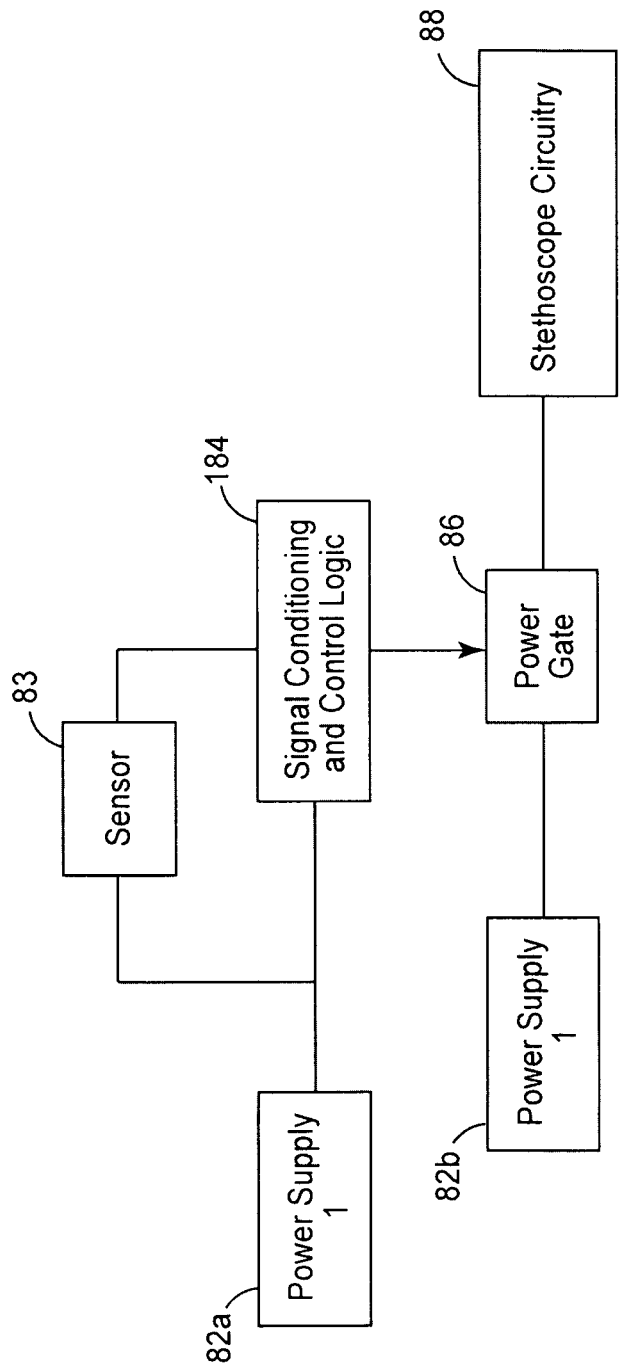

FIG. 12 illustrates an embodiment of electronic stethoscope circuitry that employs multiple power sources. In FIG. 12, a first power source 82a is configured to provide power to a first set of components, and a second power source 82b is configured to provide power to a second set of components. The first power source 82a may be a low-power device, such as a low-power battery or a storage capacitor, that is used to provide minimal power the sensor 83 and any other circuitry operating in sleep mode that is required to support the sensor 83 and production of an activation or wake-up signal. For example, the first power source 82a could rely on power supplied to the stethoscope in a manner discussed previously or over an RF link, in the manner consistent with energizing certain types of RFID devices.

The second power source 82b may be a high-power battery that provides power to the stethoscope circuitry 88 in response to sensing imminent clinician need for stethoscope usage. The embodiment illustrated in FIG. 12 provides for a low-power device with a separate battery source/storage capacitor to be used to determine the operational state of a second circuit (with greater functionality and power consumption) that has an independent power source.

As was discussed previously, a control system of the present invention may provide advanced operating mode management in addition to power management. For example, an electronic stethoscope of the present invention may incorporate a perceptible indication of the electronic stethoscope's operating status, such as by use of one or more flashing LEDs. Table 1 below provides an non-exhaustive non-limiting listing of LED illumination scenarios that may be used to convey valuable information to the clinician.

TABLE 1

| LED state | Stethoscope state |
| --- | --- |
| Flashing 1/10 or 1/6 sec | Scope on (Also timer for manually taking pulse rate) |
| LED off | Scope off |
| Flash at low rate or unique color | Low pass filter (Bell) |
| Flash at high rate or unique color | High pass filter (Diaphragm) |
| Flash both sides or alternate sides of 'split ring switch' | Special ($3^{rd}$) filter applied |
| Unique flash rate and color on LED | Visual indicate low battery |
| Remote visibility (e.g. LED on chestpiece and in yoke area) | Visual indicator pwr on/off. Fiber optic to use one light source visible in multiple areas. |

In the description of the various embodiments provided above, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention. It is further understood that systems, devices or methods according to the present invention may include one or more of the features, structures, methods, or combinations thereof described herein. For example, a device or system may be implemented to include one or more of the advantageous features and/or processes described above. It is intended that such device or system need not include all of the features described herein, but may be implemented to include selected features that provide for useful structures and/or functionality.

Figure 13:
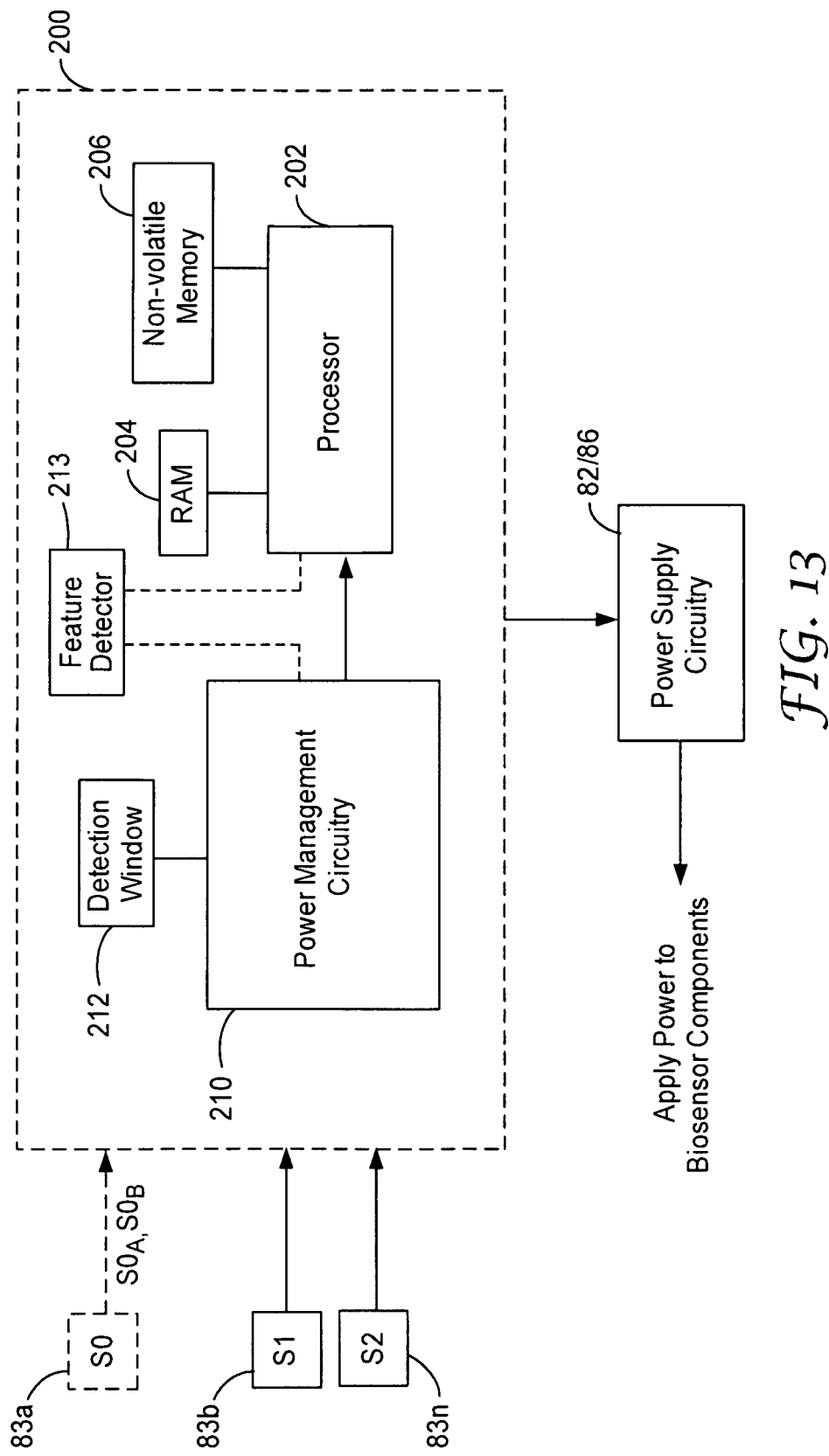
FIG. 13 is a block diagram of circuitry for implementing power management methodologies for a biosensor in accordance with embodiments of the present invention.

FIG. 13 is a block diagram of circuitry for implementing power management methodologies for a biosensor implemented in accordance with embodiments of the present invention. The circuitry 200 shown in FIG. 13 includes a processor 202 coupled to power management circuitry 210. The processor 202 includes or is coupled to random access memory (RAM) 204 (e.g., DRAM) and non-volatile memory 206 (e.g., Flash memory). The non-volatile memory 206 stores various data necessary for the operation of the biosensor, including programmed instructions executable by the processor for coordinating power management functions of the biosensor. As will be discussed below, executable program instructions are typically transferred from the non-volatile memory 206 to RAM 204 for execution by the processor 202 under predetermined conditions, such as in response to actuation of a power-on button of the biosensor by the clinician or by a command signal. Such programmed instructions in the RAM 204 are lost upon removal of power to the RAM 204, such as when an extended period of biosensor non-use is detected by the power management circuitry 210 and/or the processor 202.

The power management circuitry 210 is shown coupled to at least a first sensor 83b (S1) and a second sensor 83n (S2) of the biosensor. According to some embodiments, sense signals produced by two or more sensors 83a-n are communicated to the circuitry 200 and used by the circuitry 200 to discriminate between intended use and unintended use of the biosensor by the clinician. According to other embodiments, a single sensor or sensing device 83a (S0) is capable of sensing multiple parameters or events indicative of clinician intent for immediate usage of the biosensor. This single sensor or sensing device 83a (S0) generates a signal having two or more features ($S0_A$, $S0_B$) or signal components that are detectable by the circuitry 200 and used to discriminate between intended use and unintended use of the biosensor by the clinician. The power management circuitry 210 and the processor 202 cooperate to control power supplied to biosensor components based on the state of the first and second sensor signals (S1 and S2) produced by sensors 83b and 83n or of the two or more features or signal components ($S0_A$, $S0_B$) of a signal produced by sensor 83a (S0).

According to some embodiments, the temporal order of sensor signals S1 and S2 or signal features/components $S0_A$, $S0_B$ as received/detected by the power management circuitry 210 may be used to discriminate between intended use and nonuse of the biosensor by the clinician. Depending on the type sensor(s) employed by the biosensor, a detection window 212 may be used by the power management circuitry 210 to require a particular sequence of sensor signals or feature/components in order to distinguish between intended use and nonuse of the biosensor by the clinician. Detection of a predetermined order of the sensor signals or features/components as received by the power management circuitry 210 will satisfy the detection window's predetermined order criteria, which is indicative of intended use of the biosensor by the clinician.

A time duration between receiving/detection of sensor signals S1 and S2 or signal features/components $S0_A$, $S0_B$ by the power management circuitry 210 may also be used to discriminate between intended use and unintended use of the biosensor by the clinician. The detection window 212, according to this embodiment, may be programmed with a predetermined window duration. The detection window 212 opens in response to receiving/detecting a first sensor signal or signal feature/component, which initiates a timer of the detection window 212. If a subsequent sensor signal or signal feature/component (or multiplicity of same) is received/detected before termination of the detection window 212 (i.e., expiration of the timer), then the detection window's detection criteria is deemed satisfied, which is indicative of intended use of the biosensor by the clinician. In some embodiments, both temporal order and time duration detection may be implemented by the power management circuitry 210 to facilitate discrimination between intended use and nonuse of the biosensor by the clinician.

Figure 14:
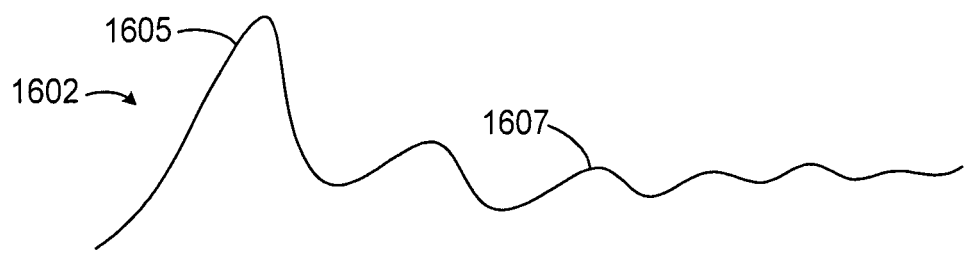
FIGS. 14-16 show signals produced by sensors of the present invention that are capable of sensing multiple parameters or events, the sensors producing a signal that has a multiplicity of features corresponding to the multiple parameters or events that are detected by power management circuitry for purposes of discriminating between intended and unintended use of a biosensor by the clinician.
Figure 15:
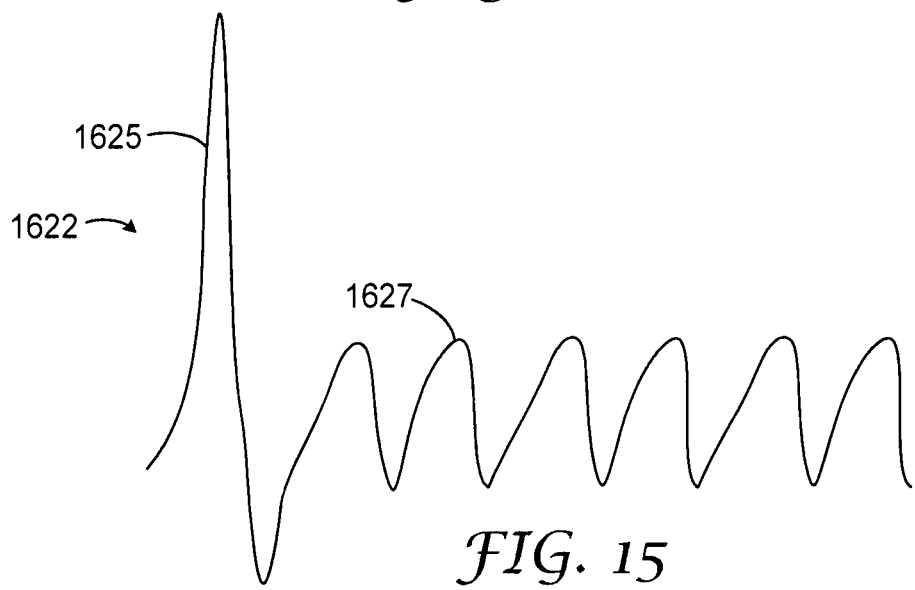
Figure 16:
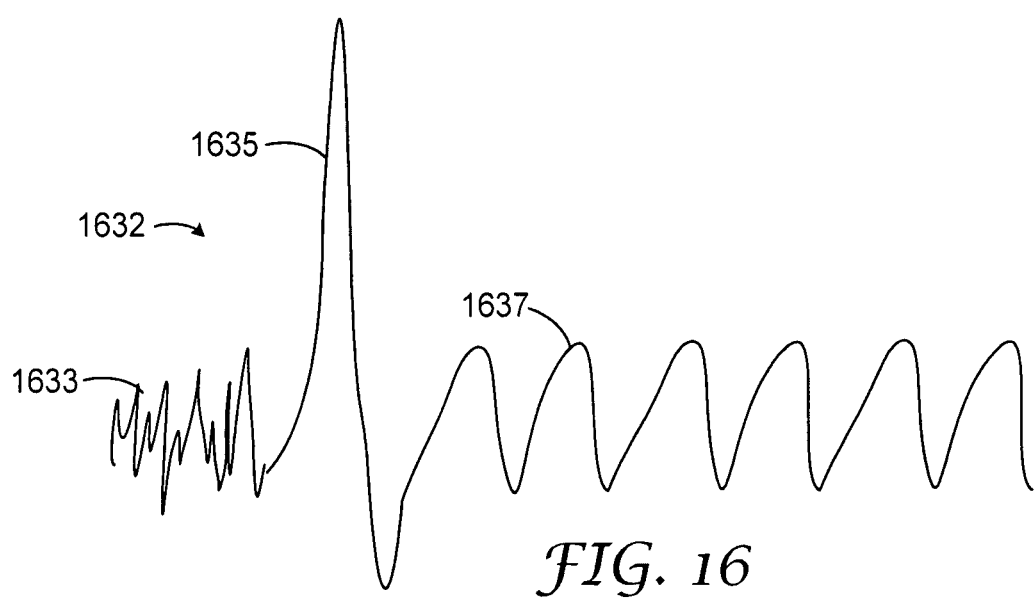

In some embodiments, a feature detector 213 may be used by the power management circuitry 210 or the processor 202 to detect features of a sensor signal for distinguishing between intended use and nonuse of the biosensor by the clinician. The feature detector 213 may, for example, detect a transient portion of a sensor signal and a non-transient portion of the sensor signal. FIGS. 14-16 show signals produced by various sensors that have a multiplicity of features corresponding to sensed parameters or events that can be detected by the power management circuitry 210 or the processor 202. FIG. 14 shows a sensor signal 1602 having a transient portion 1605 and a non-transient portion 1607. The transient portion 1605 is typically indicative of sensor proximity to or contact with a body surface or clothing of a patient or clinician. The non-transient portion 1607 represents an ongoing or persistent (e.g., steady-state) portion of the signal 1602, which may be indicative of a physiologic parameter (e.g., biopotential) or a non-physiologic or physical parameter (e.g., a change in biosensor housing temperature due to clinician/patient temperature, pressure applied to the biosensor when grasped, or a capacitance or impedance change when grasped).

FIG. 15 shows another sensor signal 1622 having a transient portion 1625 and a non-transient portion 1627. The transient portion 1625 of signal 1622 of FIG. 15 has a greater amplitude and shorter pulse width than that shown in FIG. 14. This difference is typically due to the response characteristics of the sensor employed and/or the parameter being sensed. For example, the waveform shown in FIG. 14 may be characteristic of a signal produced by a sensor that senses temperature, pressure or other parameter that changes moderately in terms of amplitude or other characteristic over time (e.g., slower response characteristics). The waveform shown in FIG. 15 may be characteristic of a signal produced by a sensor that senses acoustic emissions, acceleration, or other parameter that changes quickly in terms of amplitude or other characteristic over time (e.g., faster response characteristics), such as a heart beat.

In one embodiment, the sensor used to discriminate between intended and unintended use of the biosensor comprises the transducer of the biosensor that is used to evaluate the patient. For example, the sensor signal 1622 of FIG. 15 may represent the output of a biosensor transducer that is configured to sense a manifestation of acoustic energy produced by matter of biological origin. In this illustrative example, the transient portion 1625 of the transducer signal 1622 is representative of physical contact between the biosensor and the patient's body surface or clothing. The non-transient portion 1627 is representative of the manifestation of acoustic energy produced by matter of biological origin, such as acoustic energy produced by cardiac activity or lung activity.

FIG. 16 shows another sensor signal 1632 having a first portion 1633, a transient portion 1635, and a non-transient portion 1637. In this embodiment, the feature detector 213 is configured to detect three features of the sensor signal 1632 each indicative of a different parameter or event. The first portion 1633 of the waveform 1632 may be indicative of clinician manipulation of the biosensor, such as jostling of the biosensor when being removed from a lab coat pocket or a protective covering. The transient portion 1635 is typically indicative of contact between the biosensor and the patient's body surface or clothing. The non-transient portion 1637, in this illustrative embodiment, represents a period physiologic signal acquired from the patient, such as cardiac activity or respiration.

The feature detector 213 may use one or more known techniques for detecting signal features or components, including template matching techniques, threshold detection, determining timing of signal features (e.g., duration between signal peaks), detecting periodicity and/or randomness, signal or feature morphology analysis, frequency spectrum analysis, power spectrum analysis, and pattern or feature recognition, among others. This methodology of detecting a multiplicity of signal features or components of a sensor signal is of particular benefit when using a single sensor or sensing device to detect multiple parameters, conditions, or events.

In some embodiments, the feature detector 213 may store data corresponding to a predefined sensor profile that characterizes an excitation response of a particular sensor. For example, an sensor profile may be developed for a piezoelectric transducer or an accelerometer that characterizes the sensor's response to predetermined stimuli. The predetermined stimuli are preferably representative of real-world stimuli, such as clinician contact/manipulation events, patient contact events, and physiologic and non-physiologic stimuli. Characteristics of the sensor's response to such stimuli can be categorized as indicators of intended use or nonuse of the biosensor. Categorization of a sensor's response characteristics may be binary (i.e., intended vs. artifact) or can have gradation, such as weighting factors indicating the likelihood of intended use vs. nonuse. During operation, a condition or event sensed by a given sensor results in production of a sensor signal that can be compared to the sensor's predefined profile. Results of the comparison can be used by the feature detector 213, along with other consideration such as temporal order and/or duration of signal features, to distinguish between intended use and nonuse of the biosensor by the clinician.

Table 2 below provides a non-exhaustive, non-limiting listing of operational scenarios in which conditional power management logic may be implemented by a biosensor of the present invention, such as an electronic stethoscope. The operational scenarios implicated in Table 2 include powering-up of a biosensor by a clinician, detecting non-use of the biosensor after being used by the clinician, and implementation of an auto-On/Off methodology by which one or more sensor signals are acquired and processed by the biosensor to distinguish between intended use and nonuse of the biosensor by the clinician.

TABLE 2

| | Power Management Logic | Step | PS1 | PS2 | PS3 | PS4 | Processor (Power) | Other Components (Power) |
|---|---|---|---|---|---|---|---|---|
| (1) | Pwr Button ON | | X --- | ------ | ->Y | | Apply | Apply |
| (2) | Pwr Button ON plus XCVR | | X --- | ------ | ------ | -->Y | Apply | Apply |
| (3a) | Non-Use Detection Logic | Time $T_0$ | | | | X | Apply | Apply (incl. XCVR) |
| (3b) | | After $T_1$ | | | Y <- | --X | Apply | Apply (except XCVR) |
| (3c) | Auto-On/Off Logic Active for Y = PS2 | After $T_2$ | | Y <- | --X | | Not Apply | Not Apply |
| (3d) | Auto-On/Off Logic | After $T_3$ | Y <- | --X | | | Not Apply | Not Apply |
| (4) | S1 AND S2 = 1 | | | | X---- | ->Y or Y | Apply | Apply |
| (5) | S1 OR S2 = 1 | A | | X | | | Not Apply | Not Apply |
| | S1 AND S2 = 1 | B | | | X---- | ->Y or Y | Apply | Apply |
| (6) | S1 OR S2 = 1 | A | | X | | | Apply | Not Apply |
| | S1 AND S2 = 1 | B | | | X---- | ->Y or Y | Apply | Apply |
| (7) | S1 or S2 = 1 [w/ (6) logic] | A | | X | | | Not Apply [Apply] | Not Apply |
| | S1 AND S2 = 1 within Window | B | | | X---- | ->Y or Y | Apply | Apply |
| (8) | S1 = 1 before S2 = 1 [w/ (6) logic] | A | | X | | | Not Apply [Apply] | Not Apply |
| | S1 AND S2 = 1 | B | | | X---- | ->Y or Y | Apply | Apply |
| (9) | S1≠1 before S2 = 1 [w/ (6) logic] | A | | X | | | Not Apply [Apply] | Not Apply |
| | S1 AND S2 | B | | X | | | Not Apply | Not Apply |

Legend:
Step = Step in the Logic Flow or an Event
X = Starting State;
Y = Ending State
Arrowed Dashed Line indicates Direction of Power State Transition
PS1 = Full Power Off State
PS2 = Sleep Mode State
PS3 = Active Mode State
PS4 = Transceiver ON State
Power Management Profile may be Applicable In scenario (1) shown in Table 2 above, the clinician initiates use of the biosensor by actuating a power-On button, which transitions the biosensor from power state PSI (full power Off state) to power state PS3 (active mode state). Power is supplied to the processor and other components that enable full operational functionality of the biosensor. Scenario (2) involves transitioning the biosensor from power state PS1 to power state PS4 (transceiver On state), whereby power is also supplied to the transceiver of the biosensor (e.g., Bluetooth or ZigBee transceiver).

When the biosensor is powered on by the clinician, programmed instructions for carrying out biosensor operations, including power management operations, are transferred from non-volatile memory to random access memory (RAM) for execution by the biosensor's processor. These programmed instructions preferably remain resident in RAM until the clinician powers down the biosensor using a power-Off button or when the biosensor detects an extended period of non-use that is indicative of non-use (e.g. no use of one hour). Importantly, programmed instructions for implementing auto-On/Off detection features of the biosensor remain resident in RAM to enable transition of the biosensor from a low power state to an immediate operational state with minimal delay when intended use of the biosensor by the clinician is detected.

The manner in which the biosensor powers up may be initially based on default programming, but is preferably defined or modified by the clinician based on clinician preference. A power management profile may be established by the clinician that defines various power management functions and settings that are tailored to the clinician's preferences. For example, if the clinician generally uses a wireless transceiver functionality of the biosensor, then the clinician may predefine power state PS4 as the initial power state, rather than PS3. The power management profile may be dynamic, in that a history of biosensor power consumption may be used to define or refine parameters affecting the power management logic implemented by the biosensor. For example, if historical power usage data indicates that a clinician often sets down the biosensor for periods of 8-10 minutes between uses, the non-use detection time durations used by the power management logic to detect non-use of the biosensor (e.g., time durations $T_1$, $T_2$, $T_3$ in Table 2 above) may be adjusted accordingly to better reflect the clinician's actual history of biosensor use.

The clinician may further define preferences that tailor power management features, such as auto-On/Off detection features, to enhance usage of the biosensor by the clinician. These programmable or selectable features may include timing durations for detecting non-use of the biosensor, sequence of power-up and power-down stages, and the number of sensors used as inputs to the conditional power management logic. It may be desirable for the processor to power down to a low duty cycle state, rather than fully powering down, which may be a selectable or programmable feature made available to the clinician. The clinician may program or select various preferences concerning the sensor(s) that generate signals used by the conditional power management logic, including detection thresholds, temporal order of sensor signal requirements, time duration between sensor signals, sensor signal features, and other aspects of the sensors and/or sensor signal detection characteristics, among others.

Scenario (3) shown in Table 2 illustrates conditional power management logic for detecting non-use of the biosensor (after use by the clinician). In scenario (3$a$), time $T_0$ represents the time at which clinician use of the biosensor was last detected. A timer is initiated that begins at time $T_0$ and expires at time $T_1$. Until time $T_1$ is reached, the biosensor remains in active mode state PS3 (power to components except for the transceiver) or PS4 (power to components including the transceiver). Scenario (3$a$) show the biosensor operating in active mode state PS4 until time $T_1$ is reached, which causes the power management circuitry to transition from power state PS4 to power state PS3, which is shown as scenario (3$b$). In this case, power is removed from the biosensor's transceiver but remains applied to the processor. It is understood that if clinician use is detected before time $T_1$, the power state of the biosensor remains at active mode state PS4 and the timer is reset to zero.

In scenario (3$c$), clinician non-use continues and the timer continues to run until time $T_2$ is reached, which causes the power management circuitry to transition from power state PS3 to power state PS2 (sleep mode state). In this case, power is removed from the biosensor's processor and the transceiver. It is understood that if clinician use is detected before time $T_2$, the power state of the biosensor returns to active mode state PS4, in this illustrative example, and the timer is reset to zero. When power state PS2 is reached, the Auto-On/Off logic is enabled, scenarios of which are illustrated in scenarios (4)-(9).

In scenario (3$d$), clinician non-use continues while in power state PS2 (Auto-On/Off logic enabled) and the timer continues to run until time $T_3$ is reached, which causes the power management circuitry to transition from power state PS2 to power state PS1 (full power Off state). In this case, power is removed from all biosensor components other than those required to enable manual turn-on of the biosensor, such as by clinician actuation of a power-On button. It is understood that if clinician use is detected before time $T_3$, the power state of the biosensor is managed by the auto-On/Off logic implemented by the power management circuitry of the biosensor.

A typical time duration between times $T_0$ and $T_1$ is 2-3 minutes. A typical time duration between times $T_1$ and $T_2$ is 2-5 minutes. A typical time duration between times $T_2$ and $T_3$ is on the order of many minutes, such as 45-60 minutes. It is understood that these time durations are for illustrative purposes only, and that these time durations may be programmed by the clinician as desired.

The auto-On/Off logic scenario (4) is a fairly simple scenario, in which two sensor signals or features/components of a sensor signal (S1 and S2) are detected by the power management circuitry. Detection of S1 and S2 by the power management circuitry is indicated as a "1" state, while non-detection of S1 or S2 may be indicated as a "0" or "≠1" state. Power management circuitry applies a logical AND operation to S1 and S2 in logic scenario (4). If S1 AND S2=1, then the biosensor transitions from power state PS2 to PS3 or PS4, depending on which power state (PS3 or PS4) was initially operative or as dictated by the clinician's power management profile.

In the auto-On/Off logic scenarios (5) and (6), compound conditional logic is applied in two logic steps A and B. In logic step A of scenario (5), the power state is PS2 and S1 OR S2=1. In this illustrative example, it is unimportant which of S1 and S2 is sensed in logic step A. In response to satisfaction of the condition S1 OR S2=1, the power state remains at PS2 with no power applied to either the processor or the transceiver. In logic step B of scenario (5), the condition S1 AND S2=1 is satisfied some time after satisfaction of logic step A. In response to satisfaction of condition S1 AND S2=1 in logic step B, the biosensor transitions from power state PS2 to PS3 or PS4 (depending on which power state was initially operative or as dictated by the clinician's power management profile), and power is applied to the processor and, if PS4 applies, to the transceiver.

The auto-On/Off logic scenario (6) is similar to that of scenario (5), but results in a different power-up sequence. In logic step A of scenario (6), the power state is PS2 and S1 OR S2=1. As in scenario (5), it is unimportant which of S1 and S2 is sensed in logic step A of scenario (6). In response to satisfaction of the condition S1 OR S2=1, the power state remains at PS2 with no power applied to the transceiver. However, power is supplied to the processor in response to satisfaction of logic step A. This allows the processor to perform various operations, such as activating the other of senor S1 and S2 and implementing auto-On/Off logic. In logic step B of scenario (6), the condition S1 AND S2=1 is satisfied some time after satisfaction of logic step A. In response to satisfaction of condition S1 AND S2=1 in logic step B, the biosensor transitions from power state PS2 to PS3 or PS4 (depending on which power state was initially operative or as dictated by the clinician's power management profile), and, if PS4 applies, to the transceiver.

In the auto-On/Off logic scenario (7), a detection window is employed to detect the presence or non-presence of two sensor signals or features/components of a sensor signal (S1 and S2) within the detection window. In this scenario, the detection window is satisfied with both S1 and S2 are detected within a duration of time defined by the detection window.

In logic step A of scenario (7), the power state is PS2 and S1 OR S2=1. In this illustrative example, it is unimportant which of S1 and S2 is sensed in logic step A of scenario (7). In response to satisfaction of the condition S1 OR S2=1, power is not applied to the transceiver. Power may or may not be applied to the processor depending on programming preferences (as in the differing cases of logic scenarios (5) and (6)). In logic step B of scenario (7), the condition S1 AND S2=1 is satisfied some time after satisfaction of logic step A and only if this condition is satisfied within the time duration defined by the detection window. In response to satisfaction of condition S1 AND S2=1 within the detection window in logic step B, the biosensor transitions from power state PS2 to PS3 or PS4 (depending on which power state was initially operative or as dictated by the clinician's power management profile), and, if PS4 applies, to the transceiver.

In the auto-On/Off logic scenarios (8) and (9), a temporal order of detection of S1 and S2 is important. In this scenario, a temporal order criterion is satisfied when S1 is detected before S2. In logic step A of scenario (8), the power state is PS2 and S1 is detected before S2. In response to satisfaction of logic step A, power is not applied to the transceiver. Power may or may not be applied to the processor depending on programming preferences (as in the differing cases of logic scenarios (5) and (6)).

In logic step B of scenario (8), the condition S1 AND S2=1 is satisfied some time after satisfaction of logic step A. In response to satisfaction of logic step B, the biosensor transitions from power state PS2 to PS3 or PS4 (depending on which power state was initially operative or as dictated by the clinician's power management profile), and, if PS4 applies, to the transceiver.

In logic scenario (9), the temporal order criterion is not satisfied (i.e., S1 is not detected before S2). In response to non-satisfaction of logic step A, power is not applied to the transceiver and, depending on power management preferences, power may or may not be applied to the processor when either of S1 and S2 is detected. Even if logic step B is later satisfied (i.e., S1 AND S2 detected), the temporal order criterion of logic step A predominates and, as such, the power state remains at PS2 with power removed from the processor and the transceiver.

It is important that the logic scenarios (8) and (9) be time-limited to prevent latching of the logic in power state PS2 due to non-satisfaction of the temporal order criterion. For example, if logic scenario (9) becomes satisfied, the logic states of S1 and S2 should be reset after a reasonable time duration to allow for later satisfaction of logic scenario (8). This time duration should be relatively short ensure that detection of actual intent by the clinician to use the biosensor is not unduly delayed.

According to some embodiments, some or all of the conditional power management logic implemented by the biosensor may be disabled in response to a command signal. The command signal may be produced by actuation of a button on the biosensor or by an external device or system. There may be scenarios where the non-use detection logic and/or the auto-On/Off logic is not desirable, such as when conducting long duration research with the biosensor that may be undesirably interrupted by automatic changes made to the power state of the biosensor.

Figure 17:
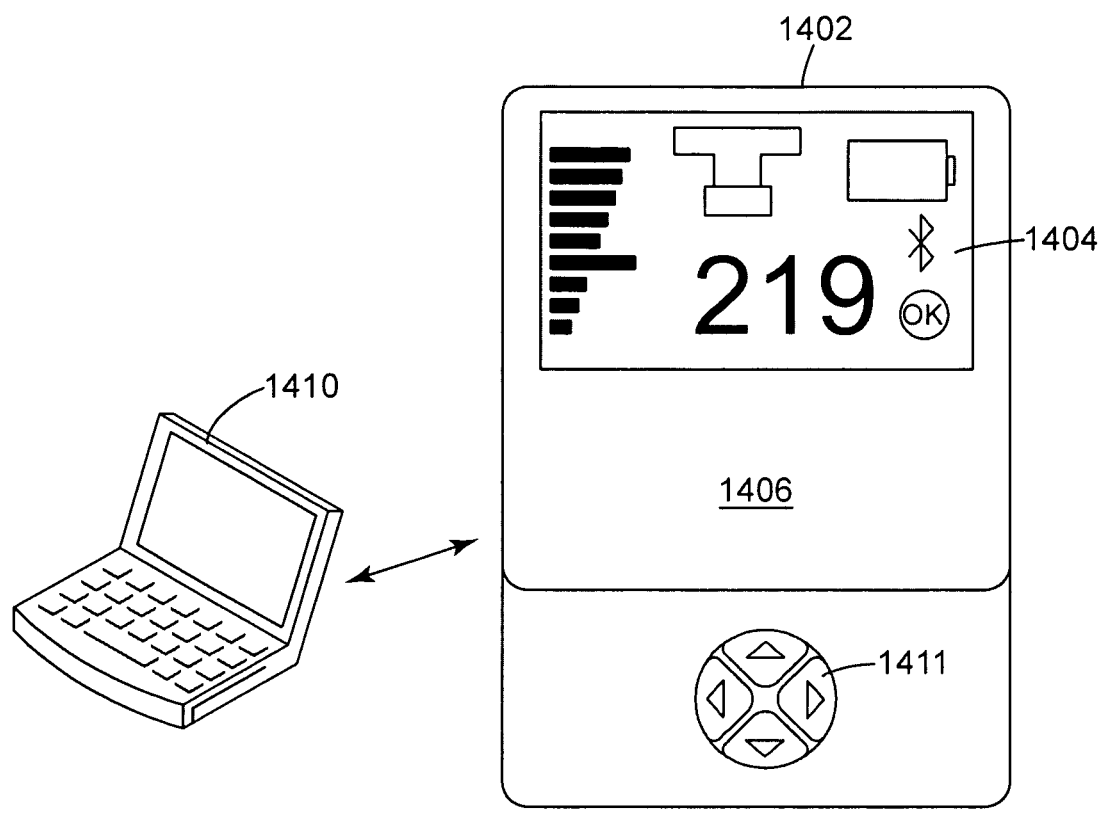
FIG. 17 shows a user interface of a biosensor, such as an electronic stethoscope, that includes a display and a multi-function control button, the display providing status and mode information about the biosensor and the patient in accordance with embodiments of the present invention.

Turning now to FIG. 17, there is shown a user interface of a biosensor, such as an electronic stethoscope, that includes a display and a multi-function control button in accordance with embodiments of the present invention. The user interface 1402 includes a display 1404 that provides status and mode information about the biosensor and the patient. Various information may be presented in textual, numerical or graphical form or a combination thereof. Various information may be communicated aurally, such as by use of tones, beeps, or electronic voice output via a speaker.

For example, amplitude or strength of the transducer signal may be shown in bar form as is commonly used in mobile communication devices or in some other form on the display 1404. Frequency related amplitude information may be shown or superimposed over the signal strength information. Battery status may be indicated graphically or in some other form, such as time remaining to depletion. The status of the biosensor's wired or wireless communication transceiver may be indicated, such as by use of a standard Bluetooth (on/off) indicator. Pairing status between the biosensor and external device 1410 may be displayed on the display 1404. The filter mode of the biosensor (e.g., bell or diaphragm mode of an electronic stethoscope) may be displayed on display 1404.

Operational status of the biosensor may be indicated by a graphical or textual indicator, such as an OK/Error indicator. Status of the patient may also be determined by the biosensor or an external system in communication with the biosensor, and this status information may be presented on the display 1404 to indicate that the patient of OK or that an anomaly has been detected. A waveform indicative of the transducer signal may be graphically presented on the display 1404, such as in display portion 1406. A multiple function button 1411 may be provided to allow the clinician to interact with, and control functions of, the biosensor. The button 1411 preferably has a setting for turning the biosensor off and on.

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. An electronic biosensor, comprising:
a housing configured for hand-held manipulation by a clinician relative to a patient;
a transducer supported by the housing and configured to sense a manifestation of acoustic energy produced by matter of biological origin;
an output device configured to output a signal comprising signal information produced by the transducer;
a processor disposed in the housing;
a sensor; and
power management circuitry disposed in the housing and coupled to the processor and the sensor, the power management circuitry comprising detection circuitry configured to detect a plurality of features of a signal produced by the sensor, the plurality of features including at least one parameter of the clinician, the power management circuitry implementing conditional power management logic by which the power management circuitry discriminates between intended use and unintended use of the biosensor by the clinician, wherein the sensor is configured to sense a parameter indicative of sensor contact or proximity between the housing and a hand or fingers of the clinician, wherein the sensor is configured to sense at least one of temperature, capacitance, impedance, pressure, force and acceleration, the power management circuitry and the processor cooperating to control power supplied to biosensor components based on the plurality of sensor signal features.

2. The biosensor of claim 1, wherein the sensor is configured to sense a parameter of the patient and a parameter indicative of sensor proximity to a body surface of the patient or clothing of the patient.

3. The biosensor of claim 1, wherein the sensor is configured to sense a parameter of the patient and a parameter indicative of contact between the biosensor and a body surface of the patient or clothing of the patient.

4. The biosensor of claim 3, wherein the sensor is configured to sense a physiologic parameter of the patient.

5. The biosensor of claim 1, wherein the sensor is configured to sense a parameter indicative of proximity with or contact between the biosensor and the clinician and a parameter indicative of proximity with or contact between the biosensor and the patient.

6. The biosensor of claim 1, wherein the conditional power management logic discriminates between intended use and unintended use of the biosensor based at least in part on a temporal order of the transient and non transient signal portions.

7. The biosensor of claim 6, wherein the sensor is configured to sense a parameter indicative of sensor proximity to a body surface of the patient or clothing of the patient.

8. The biosensor of claim 6, wherein the sensor is configured to sense a parameter indicative of sensor contact with a body surface of the patient or clothing of the patient.

9. The biosensor of claim 1, wherein the sensor comprises the transducer of the biosensor.

10. The biosensor of claim 9, wherein the sensor is configured to sense a transient portion of a signal indicative of the acoustic energy produced by matter of biological origin and a non-transient portion of the signal indicative of the acoustic energy produced by matter of biological origin.

11. The biosensor of claim 1, wherein the power management circuitry discriminates between intended and unintended use of the biosensor by the clinician based at least in part on a comparison of the sensor signal to a predefined sensor profile that characterizes an excitation response of the sensor.

12. The biosensor of claim 1, wherein the sensor comprises a single sensor element.

13. The biosensor of claim 1, wherein the sensor comprises a plurality of sensor elements.

14. The biosensor of claim 1, wherein the power management circuitry and processor cooperate to control application and removal of power respectively to and from the biosensor components based on the sensor signal features.

15. The biosensor of claim 1, wherein the processor is coupled to volatile memory and non-volatile memory, the non-volatile memory configured to store programmed instructions executable by the processor for facilitating operation of the biosensor by the clinician, the programmed instructions transferred from the non-volatile memory to the volatile memory for execution by the processor in response to a command signal.

16. The biosensor of claim 1, wherein the power management circuitry discriminates between intended and unintended use of the biosensor by the clinician based on a time duration between sensing of the respective sensor signal features.

17. The biosensor of claim 1, wherein the power management circuitry disables implementation of some or all of the conditional power management logic in response to a command signal.

18. The biosensor of claim 1, wherein the power management circuitry implements or modifies biosensor power management in accordance with a predefined power management profile selectable by the clinician.

19. The biosensor of claim 1, wherein the power management circuitry implements or modifies biosensor power management in accordance with an adaptive power management profile based on a history of biosensor power consumption.

20. The biosensor of claim 1, comprising a headset configured to communicatively couple to the output device and convert the signal comprising signal information produced by the transducer to a user-perceivable form.

21. The biosensor of claim 1, comprising:
a first power source coupled to the power management circuitry and defining a low power source, the first power source supplying power for continuous or intermittent operation of the power management circuitry during a sleep state of the processor; and
a second power source coupled to the processor and defining a high power source relative to the first power source, the second power source supplying power for the processor to transition the processor from the sleep state to a state that facilitates use of the biosensor by the clinician.

22. The biosensor of claim 1, wherein the output device comprises a user interface that provides user-perceivable output indicative of a plurality of a power status, a transducer signal strength, wired or wireless communication link status, and an operational status of the biosensor.

23. A method of managing power in an electronic biosensor configured for hand-held manipulation by a clinician, comprising:
sensing a manifestation of acoustic energy produced by matter of biological origin;
producing an output signal representative of the sensed manifestation of acoustic energy;
receiving a sensor signal from a sensor of the biosensor, wherein the sensor is configured to sense at least one of temperature, capacitance, impedance, pressure, force and acceleration;
detecting a plurality of features of the sensor signal, the features including a parameter indicative of sensor contact or proximity between a housing of the electronic biosensor and a hand or fingers of the clinician;
discriminating between intended use and unintended use of the biosensor by the clinician; and
controlling power supplied to biosensor components based on the sensor signal features.

24. The method of claim 23, wherein controlling power supplied to biosensor components comprises controlling application and removal of power respectively to and from biosensor components based on the sensor signal features.

25. The method of claim 23, wherein the sensor is configured to sense a parameter of a patient and a parameter indicative of sensor proximity to a surface of the patient or clothing of the patient.

26. The method of claim 23, wherein the sensor is configured to sense a parameter of a patient and a parameter indicative of contact between the biosensor and the patient.

27. The method of claim 26, wherein the sensor is configured to sense a physiologic parameter of the patient.

28. The method of claim 23, wherein discriminating between intended use and unintended use of the biosensor is based at least in part on a temporal order of transient and non transient signal portions.

29. The method of claim 28, wherein the sensor is configured to sense a parameter indicative of sensor proximity to a surface of a patient or clothing of the patient.

30. The method of claim 28, wherein the sensor is configured to sense a parameter indicative of sensor contact with a surface of a patient or clothing of the patient.

31. The method of claim 23, wherein the sensor is configured to sense the manifestation of acoustic energy produced by matter of biological origin, and the sensor signal is representative of the manifestation of acoustic energy produced by matter of biological origin.

32. The method of claim 23, wherein discriminating between intended and unintended use of the biosensor by the clinician comprises comparing the sensor signal to a predefined sensor profile that characterizes an excitation response of the sensor.

33. The method of claim 23, wherein discriminating between intended and unintended use of the biosensor by the clinician is based at least in part on a time duration between sensing of the respective sensor signal features.

34. The method of claim 23, comprising disabling implementation of some or all of the conditional power management logic in response to a command signal.

35. The method of claim 23, comprising implementing or modifying biosensor power management in accordance with a predefined power management profile selectable by the clinician.

36. The method of claim 23, comprising implementing or modifying biosensor power management in accordance with an adaptive power management profile based on a history of biosensor power consumption.

37. The method of claim 23, comprising producing user-perceivable output indicative of a plurality of a power status, a transducer signal strength, wired or wireless communication link status, and an operational status of the biosensor.

38. The biosensor of claim 1, wherein the transient portion of the signal is indicative of contact with a body surface of the clinician or the clothing of the clinician.

39. An electronic biosensor, comprising:
a housing configured for hand-held manipulation by a clinician;
a transducer supported by the housing and configured to sense a manifestation of acoustic energy produced by matter of biological origin;
an output device configured to output a signal comprising signal information produced by the transducer;
a processor disposed in the housing; and
power management circuitry disposed in the housing and coupled to the processor, the power management circuitry coupled to at least a first sensor and a second sensor of the biosensor respectively configured to produce first and second sensor signals, the power management circuitry implementing conditional power management logic by which the power management circuitry discriminates between intended use and non-use of the biosensor by the clinician based on a state of the first and second sensor signals, wherein one of the first and second signals is indicative of contact between the clinician's hand or fingers with a least a portion of the housing, wherein one of the at least first and second sensor signals is one of temperature, capacitance, impedance, pressure, force and acceleration, the power management circuitry and the processor cooperating to control power supplied to biosensor components based on the state of the first and second sensor signals.

40. The electronic biosensor of claim 39, wherein the first signal is indicative of clinician contact with at least a portion of the housing and wherein the second sensor signal is representative of the manifestation of acoustic energy produced by matter of biological origin.

* * * * *